United States Patent [19]

Takahashi et al.

[11] Patent Number: 4,500,412
[45] Date of Patent: Feb. 19, 1985

[54] OXYGEN SENSOR WITH HEATER

[75] Inventors: Hideaki Takahashi; Kiyoharu Hayakawa; Haruyoshi Kondo; Takashi Takeuchi, all of Aichi, Japan

[73] Assignee: Kabushiki Kaisha Toyota Chuo Kenkyusho, Aichi, Japan

[21] Appl. No.: 404,900

[22] Filed: Aug. 3, 1982

[30] Foreign Application Priority Data

Aug. 7, 1981 [JP] Japan .................................. 56-123122
Oct. 9, 1981 [JP] Japan .................................. 56-160077
Dec. 2, 1981 [JP] Japan .................................. 56-192744

[51] Int. Cl.$^3$ .......................................... G01N 27/58
[52] U.S. Cl. ..................................... 204/425; 204/408; 204/426; 204/429
[58] Field of Search ............... 204/406, 408, 424, 425, 204/426, 429, 15

[56] References Cited

U.S. PATENT DOCUMENTS

| | | | |
|---|---|---|---|
| 3,767,469 | 10/1973 | Flais et al. | 204/428 X |
| 3,948,081 | 4/1976 | Wessel et al. | 204/408 X |
| 4,071,817 | 1/1978 | Bahl | 204/15 X |
| 4,107,019 | 8/1978 | Takao et al. | 204/426 X |
| 4,277,323 | 7/1981 | Muller et al. | 204/425 |
| 4,304,652 | 12/1981 | Chiba et al. | 204/425 |
| 4,347,114 | 8/1982 | Kimura et al. | 204/426 |
| 4,365,604 | 12/1982 | Sone | 204/424 X |
| 4,407,704 | 10/1983 | Mase et al. | 204/406 X |

FOREIGN PATENT DOCUMENTS 30164  6/1981  European Pat. Off. ............ 204/427

Primary Examiner—G. L. Kaplan
Assistant Examiner—Nam X. Nguyen

[57] ABSTRACT

A sensor which has an insulating substrate on which is formed a heater layer for heating the sensor on a part thereof and which is operated above a predetermined temperature. The heater layer is made of a material which has a thickness of 0.2 μm to 20 μm and which is made of platinum, rhodium, palladium or a mixture thereof. The insulating substrate is made of alumina, quartz, spinel, magnesia, zirconia, or mixtures thereof. A heater protective layer having a thickness of 0.01 μm to 500 μm is made of materials based on alumina, silica, spinel, magnesia, zirconia or mixtures thereof.

16 Claims, 54 Drawing Figures

FIG. 1A
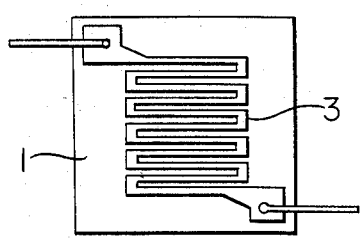
FIG. 1B
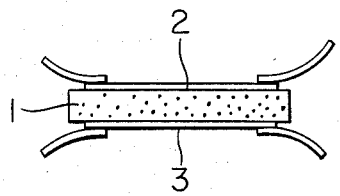
FIG. 1C
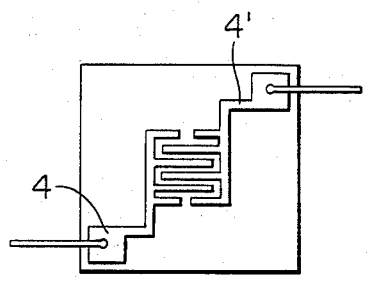
FIG. 2
(a) 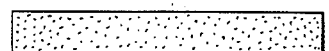
    $Al_2O_3$ SUBSTRATE
    ↓
    $Nb_2O_5 \cdot Pt$ SPUTTERING
    ($\sim 1000 [Å]$)
(b) 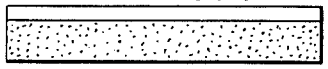
    ↓
                    PHOTORESIST MASKS
(c) 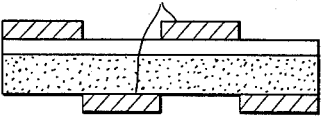
    ↓
    Pt SPUTTERING ($\sim 1 [\mu m]$)
(d) 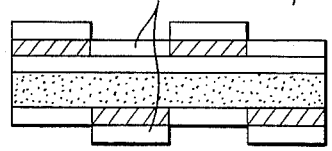
    ↓
(e) CUTTING
    ↓
(f) PEELING OFF
    PHOTORESIST MASKS
    ↓
    Pt LEAD WIRE $\phi$ 50 [$\mu m$]
(g) (THERMOCOMPRESSION
    BONDING METHOD)

OXYGEN SENSOR WITH HEATER

BACKGROUND OF THE INVENTION

I. Field of the Invention

The present invention relates to an oxygen sensor with a heater and, more particularly, to a compact oxygen sensor part of which has a heater thereon.

II. Description of the Prior Art

Some sensors among various types of sensors are kept above a predetermined temperature in use. Typical examples are an oxygen concentration cell type oxygen sensor with an oxygen ionic conductor (e.g., $ZrO_2$) and an oxygen sensor which utilizes a resistance change in an oxide semiconductor (e.g., $TiO_2$ or $CoO$). These sensors can only be used above a temperature of about 400 [°C.] due to the following reasons. When a reaction sufficiently progresses in an exhaust gas, that is, when a chemical equilibrium state is established, the oxygen partial pressure in the theoretical air-fuel ratio is abruptly changed. If the oxygen concentration cell type oxygen sensor is used, the electromotive force abruptly changes. If the oxide semiconductor type oxygen sensor is used, the resistance abruptly changes. However, in practice, a small amount of combustible components ($H_2$, CO, HC) coexists with oxygen, so that the reaction described above does not progress completely. In this condition, if a signal proportional to the oxygen partial pressure in the exhaust gas is simply produced by the sensor, the electromotive force or resistance which is based on the theoretical air-fuel ratio will not be abruptly changed. In order to eliminate the above drawback, a catalyst is used to accelerate the reaction inside the sensor or in the vicinity of the surface thereof so as to greatly change the electromotive force or resistance according to the theoretical air-fuel ratio. Therefore, the lower operating limit of the catalyst determines that of the oxygen sensor. Since the reaction acceleration effect of the catalyst cannot be obtained at temperatures of not lower than about 400 [°C.], the conventional oxygen sensor can only be used at temperatures of not lower than 400 [°C.].

Alternatively, a limiting current type oxygen sensor has been proposed which has an anode and a cathode, and a means disposed at the cathode for limiting the inflow of a gas to be measured. When a predetermined DC voltage is applied across the oxygen sensor of this type, the sensor measures a limiting current flowing therethrough to detect the oxygen concentration. However, since the internal resistance is increased at a relatively low temperature, an output proportional to the oxygen concentration cannot be obtained. Therefore, the limiting current type oxygen sensor is not suitable for measurement at low temperatures.

In order to eliminate the drawback described above, a heater must be arranged in the limiting current type oxygen sensor so as to measure the oxygen concentration at low temperatures. However, it is desirable that the heating temperature be as high as 800 [°C.] to 900 [°C.] and that power consumption be as low as about 10 [W].

Sensors are often mounted in a small space. The typical example is an oxygen sensor which measures the distribution of the air-fuel ratio in an exhaust pipe of a vehicle. A sensor of this type must be very small, and so a heater used therein must also be small in size and light in weight. Even when there is no space-limitation factor, a compact and light-weight sensor and heater are desirable.

Further, sensors are often used in severe circumstances. For example, they may be used in a gas or liquid, or in an atmosphere where temperature change is great. Heaters for heating sensors of this type must have excellent durability and must not substantially degrade over time in the severe circumstances.

Further, a change in output of a sensor occurs with a change in the ambient temperature; the sensor output depends upon temperature variation. In order to eliminate temperature dependency of the sensor, the heating power of the heater is controlled according to the sensor temperature so as to keep its temperature constant. In order to keep the sensor temperature constant even if the ambient temperature is abruptly changed, there must be substantially no time lag between the change in heating power of the heater and the resulting change in the sensor temperature; excellent response time between the variables is required.

It is also desirable that sensor heaters be capable of being mass-produced at low cost with excellent mechanical strength, and that temperature control be easy.

Conventional heating methods for heating sensors have been proposed as follows, but none of these sufficiently satisfies the above needs.

A first heating method is performed by arranging a separate heater in the vicinity of the sensor to heat the sensor.

In a clean atmospheric environment, a tungsten wire, Kanthal alloy wire or the like is simply used as the heater. In severe circumstances such as a gaseous atmosphere or an exhaust gas atmosphere, or when immersed in water, a sheath wire is used wherein a tungsten, Kanthal alloy, or nichrome wire is coated with MgO powder and is embedded in a stainless steel or Inconel pipe. However, the heater itself becomes larger in size and the power consumption of the heating is more than several tens of watts. Therefore, the heating method described above is not suitable for the sensor under discussion.

A second heating method is performed by forming a sensor integrally with a heater for efficient heating. For this purpose, there are some conventional techniques whereby, for example, the heater is embedded in the sensor, or, alternatively, a heater pattern is printed on the lower surface of a substrate by a screen printing technique. However, the first technique does not provide a compact heater, and the heater wire according to the second technique is open to the atmosphere, so that it is greatly degraded over time (especially, in a "rich" mixture of the air-fuel ratio). Further, in the currently adopted printing method, the heater can hardly be formed with dimensions smaller than 150 [μm] width and 10 [μm] thickness. Micropatterning of the heater results in a size from ten up to about twenty millimeters. Thus, the heater pattern cannot be effectively used for the sensor under discussion. Neither the first nor the second heating method can sufficiently satisfy the various characteristics described above.

SUMMARY OF THE INVENTION

It is, therefore, an object of the present invention to provide a direct-heating type oxygen sensor part of which has a heater thereon, wherein the heater for heating the sensor has a low power consumption and heats the sensor to a high temperature, such that the sensor has fast response time, excellent durability, degrades little over time and is very small in size and light in weight.

It is another object of the present invention to provide a direct-heating type oxygen sensor wherein a thin oxide semiconductor film is formed on an insulating substrate and a heater layer is formed on part of the insulating substrate by properly selecting the material, size and surface condition of a protective layer.

It is still another object of the present invention to provide a limiting current direct-heating type oxygen sensor which has a cathode on one major surface of an oxygen ionic conductor and an anode on the other major surface thereof to use the anode and the cathode as heaters by properly selecting the material, shape, size and arrangement of the anode and the cathode.

In order to achieve the above objects of the present invention, there is provided a direct-heating oxygen sensor characterized in that the heater layer has a thickness in the range of 0.2 [μm] to 20 [μm] and is made of a material selected from the group consisting of platinum, rhodium, palladium and a mixture of at least two thereof.

According to one aspect of the present invention, a detector section is formed on the insulating substrate of the oxygen sensor, and a heater layer is formed on part of the insulating substrate.

According to another aspect of the present invention, the insulating substrate is made of a material selected from the group consisting of alumina, quartz, spinel, magnesia, zirconia, and a mixture of at least two thereof.

According to still another aspect of the present invention, an indentation of 0.2 to 15 [μm] (peak-to-peak) size is formed on the surface of the insulating substrate to improve bonding between the insulating substrate and the heater layer.

According to still another aspect of the present invention, the heater layer comprises a mixture of platinum and either rhodium or palladium, and a mixing ratio of rhodium or palladium is determined to be 0 to 60 [wt %].

According to still another aspect of the present invention, the heater layer is coated with a protective layer which has a thickness of 0.01 [μm] to 500 [μm] and which is made of a material selected from the group consisting of materials based on alumina, silica, spinel, magnesia, zirconia, and a mixture of at least two thereof.

According to still another aspect of the present invention, the oxygen sensor has an oxygen partial pressure sensitive portion which is formed on one major surface of the insulating substrate and which comprises a thin film made by adding as a catalyst a material selected from the group consisting of platinum, rhodium, palladium and a mixture thereof to one of the oxide semiconductor materials (niobium pentoxide and cerium oxide). The heater layer is formed on one or the other major surface of the insulating substrate.

According to still another aspect of the present invention, there is provided an oxygen sensor wherein:

a first layer is formed on one major surface of the oxygen ionic conductor, the first layer being made of a material selected from the group consisting of platinum, rhodium, palladium and a mixture of at least two thereof and having a thickness in a range of 0.2 [μm] to 20 [μm];

a second layer is formed on the other major surface of the oxygen ionic conductor such that the second layer corresponds to the first layer with the oxygen ionic conductor interposed therebetween, the second layer being made of the same material as the first layer with the same shape and size; and a pair of lead wires are respectively connected to the first and second layers so as to use the first layer as a heater/cathode (cathode/heater) and the second layer as a heater/anode (anode/heater).

According to still another aspect of the present invention, the heater layer is used as a temperature-sensitive element. In the oxygen sensor with a constant temperature heating circuit which detects a heating temperature in order to control power to be supplied to the heater layer in accordance with the detected value so as to keep the heating temperature constant, the constant temperature heating circuit is arranged to detect the resistance of the heater layer and to control the power to be supplied to the heater layer in accordance with the detected value so as to keep the resistance of the heater layer constant.

BRIEF DESCRIPTION OF THE DRAWINGS

A more complete understanding of the invention and the various features, additional objectives and advantages thereof may be more readily appreciated and better understood by reference to the following detailed description in conjunction with the drawing.

FIGS. 1A to 1C show an oxygen sensor with a heater according to one embodiment of the present invention, in which FIG. 1A is a plan view thereof when viewed from the heater side, FIG. 1B is a side view thereof, and FIG. 1C is a plan view thereof when viewed from the side of an oxygen partial pressure sensitive thin film;

FIG. 2 shows at (a)-(g) sections for explaining the steps of manufacturing the oxygen sensor with the heater;

FIG. 9 is a graph showing dependency of an oxygen partial pressure $P_{O_2}$ upon conductivity $\doteq$, the number of excess electrons, the number of excess atoms, and so on;

DETAILED DESCRIPTION OF THE PREFERRED EMBODIMENTS

FIGS. 1A to 1C show an oxygen sensor according to one embodiment of the present invention. FIG. 1A is a plan view of the oxygen sensor when viewed from the heater side, FIG. 1B is a side view thereof and FIG. 1C is a plan view thereof when viewed from the side of the thin film sensor. A thin oxide film 2 of an oxygen partial pressure sensitive material is formed on one major surface of an insulating substrate 1. A heater layer 3 is formed on the other major surface of the insulating substrate 1. Electrodes 4 and 4' for measuring the resistance of the thin oxide film is formed on the surface of the thin oxide film 2. Further, a catalyst layer is also formed on the thin oxide film 2. A dense (nonporous) coating (not shown in FIG. 1) is formed on the heater layer 3 and a porous layer (not shown in FIG. 1) is formed on the sensor. A dense coating is also formed on lead wire connecting portions.

A method for manufacturing the oxygen sensor of this embodiment will be described with reference to FIG. 2.

(a) Prepared are an alumina ($Al_2O_3$) substrate (size: $30 \times 30 \times 0.2$ [mm]; surface finish: #320-850), sintered bodies of niobium pentoxide ($Nb_2O_5$) (110 [mm] in diameter and 8 [mm] in thickness) as a target material, and platinum (Pt) (110 [mm] in diameter and 1 [mm] in thickness).

(b) $Nb_2O_5$ is sputtered in an atmosphere of argon (Ar) by a bipolar sputtering device in a vacuum of $4 \times 10^{-2}$ [Torr] for about 20 minutes.

(c) Photoresist masks for prospective electrode regions are formed on the sputtered surface of the sintered body, while a photoresist mask for a prospective heater region is formed on the nonsputtered surface thereof. Thereafter, the structure is developed.

(d) Platinum is sputtered in an Ar atmosphere by the bipolar sputtering device in a vacuum of $4 \times 10^{-2}$ [Torr].

(e) The structure is cut into pieces (1.70×1.75 [mm] each) by a dicing machine.

(f) Each piece is dipped in a solvent (acetone) to remove the photoresist masks. As a result, a Pt heater region and Pt electrode regions are formed.

(g) Pt lead wires are connected to the electrode regions.

The heater and the electrodes are preferably made of platinum (Pt), rhodium (Rh), palladium (Pd) or a mixture thereof in consideration of material stability and temperature coefficients. If the mixture is used, the content of rhodium or palladium is preferably in a range of 0 to 60 [wt %].

Figure 3:
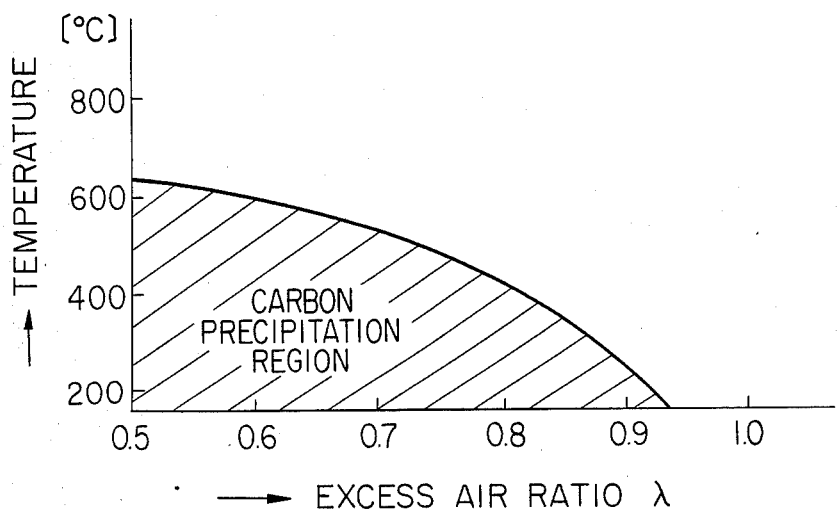
FIG. 3 is a graph showing temperature as a function of an excess air factor to show a carbon precipitation region.

It is assumed that the heater for the oxygen sensor according to the present invention is used in the exhaust gas of a vehicle engine. The adhesion of carbon and its precipitation from the gas phase must also be considered. FIG. 3 shows a carbon region precipitated from the gas phase with respect to an excess air ratio λ and to temperature when a fuel composition is $C_8H_{16}$. As may be seen from FIG. 3, the oxygen sensor must be heated above a temperature of 700 [°C.] so as not to precipitate carbon even in a very "rich" mixture represented by the excess air ratio λ being 0.6. In the precipitation region of carbon, CO in the gas phase is converted to carbon and soot is attached to the sensor, resulting in electrical shortcircuiting and hence inconvenience.

In order to guarantee the durability of the oxygen sensor in the exhaust gas at a temperature of 700 [°C.], a Pt type heater must be used.

Figure 4:
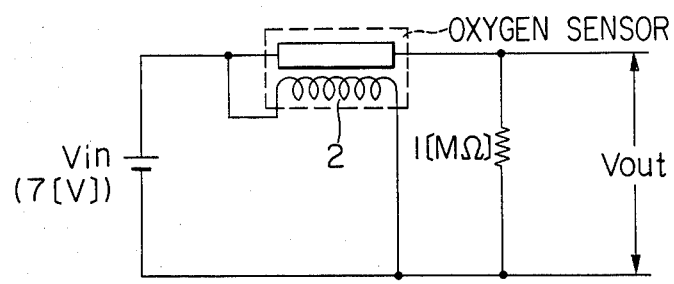
FIG. 4 is a circuit diagram of a constant voltage circuit for applying a constant voltage across the oxygen sensor with the heater.
Figure 5:
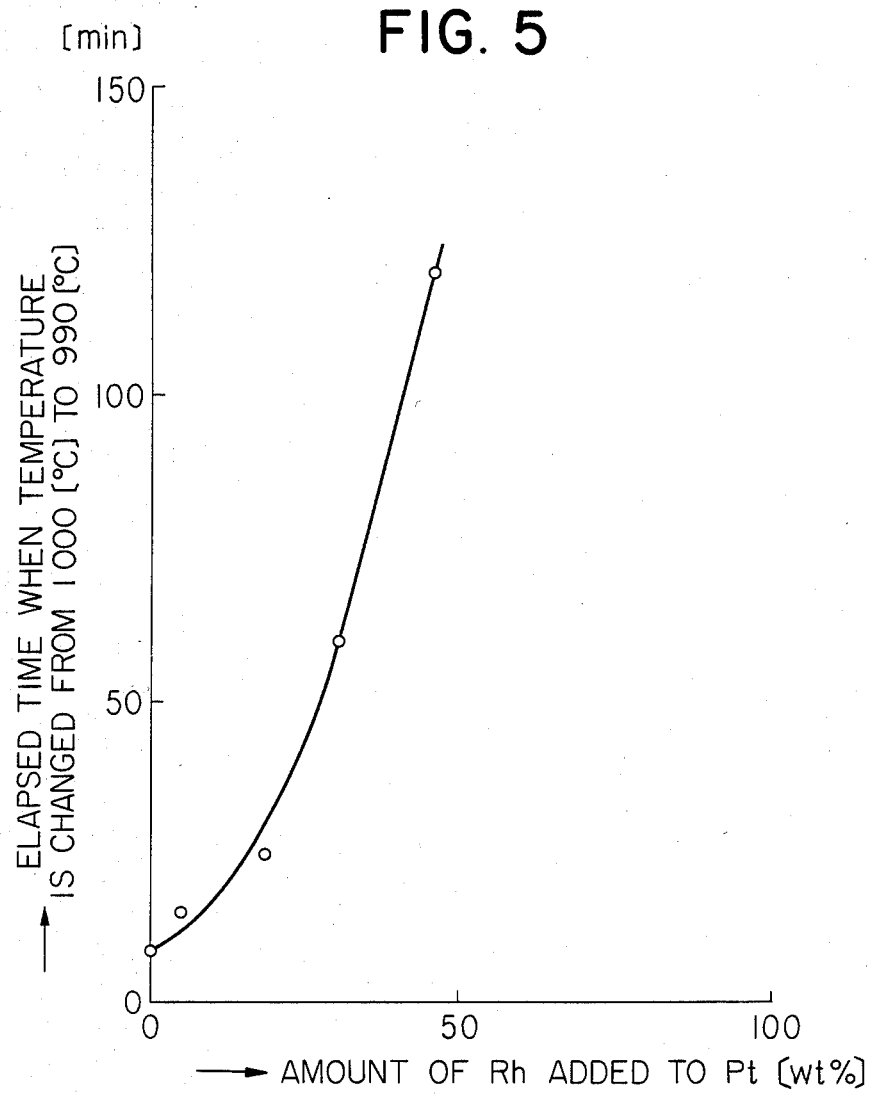
FIG. 5 is a graph showing elapsed time until temperature drops to 990 [°C.] when the heater is heated to a temperature of 1,000 [°C.] as a function of an amount of Rh added to Pt.

The present inventors have conducted an experiment in which rhodium was added to platinum, a thin film heater was formed by the sputtering device, and the stability of the thin film was examined at a temperature of 1,000 [°C.]. As shown in FIG. 4, a constant voltage was applied to the thin film heater. The time interval was measured during which the temperature dropped from 1,000 [°C.] to 990 [°C.] as a result of the resistance of the heater being increased due to its degradation. Results are shown in Table 1 and FIG. 5. As may be seen from the table and the figure, when the amount of rhodium added is increased, it is found that stability is improved. Note that thermocompression bonding between the heater and the platinum wire (50 [μm] in diameter) is degraded when the amount of rhodium added is increased.

TABLE 1

Relationships between the time interval required for the heater temperature to decrease by 10 [°C.] and the amount of Rh added to Pt in a heater made of a mixture of Pt and Rh

| Amount of Rh Added [wt %] | 0 | 5 | 18 | 30 | 45 |
|---|---|---|---|---|---|
| Time [min.] | 9 | 15 | 25 | 60 | 120 |
| Evaluation | poor | → | → | → | good |

Figure 6:
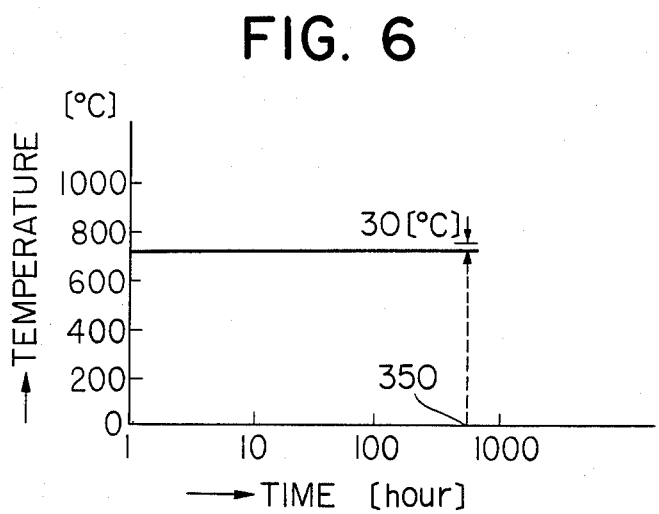
FIG. 6 is a graph showing temperature as a function of time when the heater is continuously powered by the contact voltage circuit shown in FIG. 4.

FIG. 6 shows the result of a stability test of the Pt heater at a temperature of 700 [°C.]. As may be apparent from the figure, a temperature drop of 30 [°C.] is observed over 350 [hrs], demonstrating excellent stability.

The thickness of the heater is preferably in the range of 0.2 [μm] to 20 [μm] in consideration of the stability of the resistance and the manufacturing process. The width of the heater wire is preferably 100 [μm] or less due to the following reasons.

Figure 7:
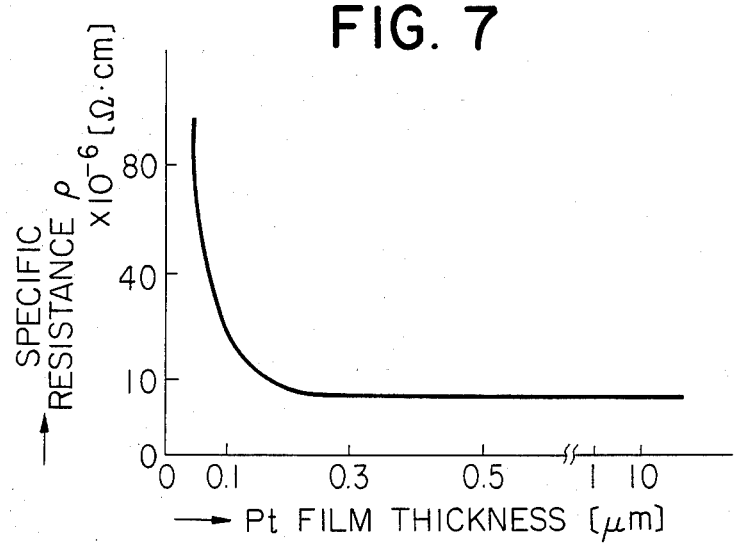
FIG. 7 is a graph showing specific resistance as a function of a Pt film thickness.

The power source voltage of the car battery is 12 [V]. In order to maintain the heater temperature at about 700 [°C.] to 800 [°C.] by a power source voltage of 12 [V], the resistance of the Pt heater cannot be set above several hundreds of ohms. Further, if the Pt film is thin, the specific resistance is greatly increased, as shown in FIG. 7. Even if the thin Pt film is heated to a temperature of not more than about 800 [°C.], the platinum film coagulates, resulting in unstable operation. However, if the film thickness is not less than 0.2 [μm], its specific resistance is not greatly changed. In a test where the film of not less than 0.2 [μm] thickness is placed in air at a temperature of 800 [°C.], the film does not significantly coagulate nor does the specific resistance significantly increase.

As is apparent from the above description, the film thickness of the heater is preferably in the range of 0.2 [μm] to 20 [μm].

The specific resistance of platinum is $9.81 \times 10^{-6}$ [Ω·cm] and its temperature coefficient α is $3.96 \times 10^{-3}/[°C.]$. Therefore, the present inventors prepared the film with a thickness of about 1 [μm] and a resistance of 35 [Ω] at a room temperature of 20 [°C.].

If an attempt is made to heat the heater to a temperature of not lower than 700 [°C.] while maintaining heater power at not less than 5 [W], the substrate dimensions must be not more than 2×2×0.2 [mm]. Further, since the car battery is the power source, the resistance of the Pt heater must not be more than several hundred ohms. In order to satisfy the above conditions, the heater wire width must not be more than 100 [μm].

The insulating substrate must be a material which has excellent mechanical strength, a resistance to electric insulation, and excellent chemical stability preventing reaction with any other material. In order to satisfy the above conditions, alumina ($Al_2O_3$) is preferred as the insulating substrate.

It is assumed above that the oxygen sensor of the present invention is used in the exhaust gas atmosphere of a vehicle engine; the oxygen sensor is further used for various combustion chambers. Therefore, the oxygen sensor is used in the temperature range of ambient temperature to 800 [°C.]. Further, vibrations may act on the oxygen sensor. In order to operate the oxygen sensor in a stable condition, the substrate must be carefully selected. Workability, heat resistance and adhesion strength with the platinum film were tested for four kinds of substrate, that is, an Si+$SiO_2$ film, a pure $SiO_2$ (quartz) plate, an $Al_2O_3$ sintered plate, and an $Al_2O_3$ monocrystalline (sapphire) plate. Testing procedures are shown below:

(1) WORKABILITY

Workability is tested by an ultrasonic process machine and a diamond cutter.

(2) HEAT RESISTANCE (2-1) Heat Resistance of Substrate

A cycle of rapid heating and cooling in air at a temperature range of 800 [°C.] to ordinary temperature is repeated five times to determine whether or not the substrates crack or distort.

(2-2) Substrate Resistance to Reaction with Platinum and Resistance of Substrate and Platinum to Atmosphere Platinum is sputtered on each substrate to prepare a thin film. The thin film is exposed in an atmosphere with an excess air ratio λ=0.7 ("rich" mixture) and in an atmosphere with an excess air ratio λ=1.5 ("lean" mixture) at a temperature of 800 [°C.] for 1 hour, so as to examine its stability. As a result, the Si+SiO$_2$ film reacts with platinum, and the silicon dioxide is reduced to silicon, so that the insulating function is lost. Therefore, the Si+SiO$_2$ film is not suitable for the substrate of the oxygen sensor of the present invention.

(2-3) Substrate Adhesion Strength to Platinum Film

Platinum is sputtered on each substrate to a thickness of 1 [μm]. The resultant film is annealed in air at a temperature of 800 [°C.] for 1 hour and is rapidly cooled to room temperature to determine whether the platinum film peels off.

Results are shown in Table 2. As is seen from Table 2, the Al$_2$O$_3$ sintered plate is chemically excellent and can be manufactured at low cost, thus practicability of this film is excellent.

TABLE 2

| Substrate Material | Characteristics | | | | | |
|---|---|---|---|---|---|---|
| | Work-ability | Heat Resistance | Adhesion With Pt Film | Thermal Stability | Cost | Overall Evaluation |
| Si + SiO$_2$ Substrate | o | x | x | x | o | x |
| Al$_2$O$_3$ Sintered Substrate | o | o | o | o | o | o |
| Quartz (SiO$_2$) Substrate | Δ | o | x | o | x | x |
| Sapphire (Al$_2$O$_3$ Monocrystalline) Substrate | x | o | x | x | x | x |

The insulating substrate is formed with identations, in terms of surface roughness, which is preferably in the range of 0.2 [μm] to 15 μm] in consideration of the film adhesion strength and of the resistance stability. In practice, the surface of the insulating substrate is preferably polished by a polishing surface of #150 to #2000.

Figure 8:
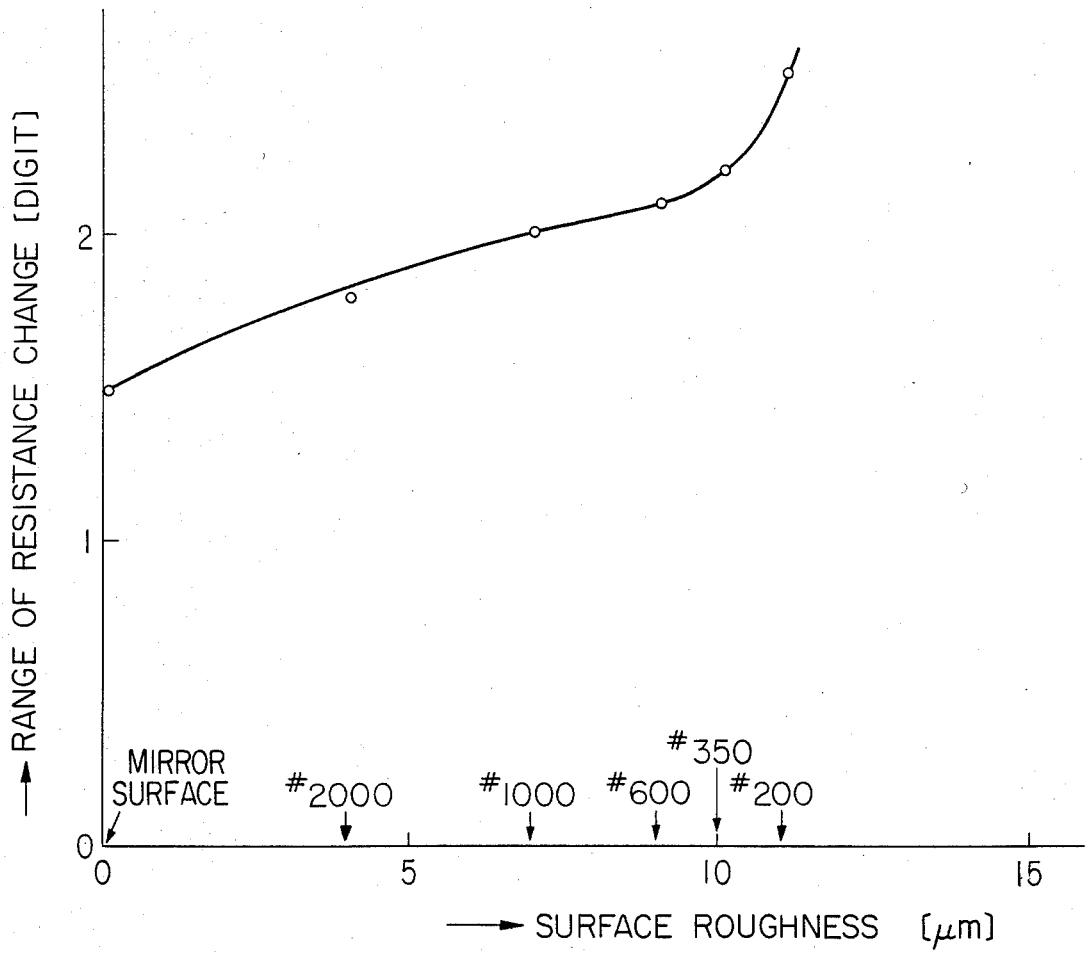
FIG. 8 is a graph showing change in resistance as a function of surface roughness of an $Al_2O_3$ substrate.

The relationship between the surface roughness of the Al$_2$O$_3$ sintered plate and the range of resistance change is tested when the "rich" mixture is changed to the "lean" mixture. Results are shown in Table 3 and FIG. 8. It is found that the range of resistance change is increased when the surface roughness is increased.

TABLE 3

| | Material | | | | | |
|---|---|---|---|---|---|---|
| | Sapphire | Al$_2$O$_3$ Sintered Body | | | | |
| Surface Roughness | | 4 [μm] (peak-to-peak) | 7 [μm] | 9 [μm] | 10 [μm] | 11 [μm] |
| Surface Finish | (Mirror Surface) | #2000 Finish (79 [μm]) | #1000 Finish (158 [μm]) | #600 Finish (28 [μm]) | #350 finish (45 [μm]) | #200 Finish (79 [μm]) |
| Range of Resistance Change (Digit) | 1.5 | 1.8 | 2 | 2.1 | 2.2 | 2.5 |
| Evaluation | Poor | → | → | → | → | Good |

However, it is difficult to form a rough surface of more than #200 while guaranteeing the mechanical strength of the substrate when the plate thickness is 0.1 [mm] to 0.2 [mm]. As a result, it is found that the indentations of the Al$_2$O$_3$ plate are preferably in the range of 0.2 [μm] to 15 [μm] (peak-to-peak).

It is also found that if the indentation size of the surface is about 5 [μm] or less, a thin layer which comprises aluminum (Al), titanium (Ti), tungsten (W), or molybdenum (Mo) formed to a thickness of about 100 [Å] to 1 [μm] between the substrate (quartz, sapphire, or Al$_2$O$_3$) and the heater layer (Pt or Pt+Rh material) greatly improves the adhesion strength between the substrate and the heater layer.

If a dense layer is formed on the surface of the heater layer, its strength is improved, and the heater layer may not be easily contaminated. Further, since the amount of a noncombustible gas to be supplied to the surface of the heater layer is limited, any temperature rise due to reaction heat is limited, so that temperature control is stably performed and the service life of the heater layer is prolonged.

A material based on alumina, silica, spinel, magnesia, or zirconia is suitable as a material of the dense layer in consideration of strength, thermal stability, and the substantial prevention of reaction with any other material.

Referring to FIG. 1 again, the heater layer and the thin film sensitive to oxygen are formed on one and the other major surfaces respectively of the insulating substrate. However, the heater layer and the thin film may both be formed on the same surface.

If they both are formed on the same surface of the insulating substrate, porous films are preferably formed thereon, whereby the thin film and the heater layer are reinforced and may not be contaminated. Further, the temperature rise due to the reaction of combustible components is decreased.

When the heater layer and another gas sensor (to be represented by a thin film sensitive to oxygen as an example) are formed on the same surface of the substrate, and when they are covered with the porous film, care must be taken in sensor operation as well as for heater protection.

The material of a thin film sensitive to an oxygen partial pressure must be selected in consideration of the applicable range of oxygen partial pressure, stability, response time, specific resistance and so on.

The applicable range of the oxygen partial pressure will be described with reference to test results.

Figure 9:
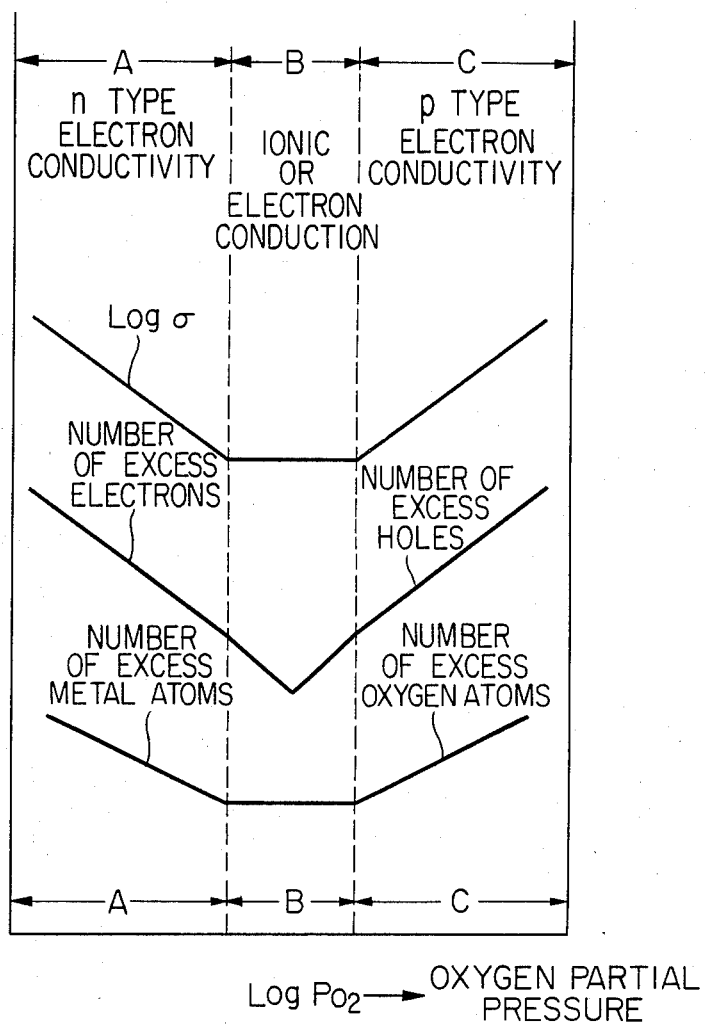

In a condition where an oxide is smoothly oxidized or reduced to reach a chemical equilibrium state between the oxide and the surrounding oxygen partial pressure, conductivity σ of the oxide substantially depends upon the oxygen partial pressure, as shown in FIG. 9. However, when an oxygen partial pressure P$_{O2}$ is sufficiently low (region A in FIG. 9), same of the oxygen atoms of the oxide are emitted outside, so that lattice defects such as an oxygen hole or a metal atom between the lattices occur. These lattice defects are ionized to emit conduction electrons, so that the oxide shows an n type conductivity. In the region A, when the partial pressure P$_{O2}$ is decreased, the number of conduction electrons is increased and the conductivity of the oxide is increased. However, when the oxygen partial pressure is sufficiently high (region C in FIG. 9), oxygen atoms in the oxide are excessive, so that lattice defects such as a metal atom hole or an oxygen atom between the lattices occur. When the lattice defects are ionized, the lattice receives an electron (actually, a hole is eliminated). As a result, the oxide has a p type conductivity. In the region B, when the oxygen partial pressure $P_{O_2}$ is increased, the hole density of the oxide is increased and its conductivity is increased. However, if the oxygen partial pressure is intermediate (region C in FIG. 9), the number of electrons (or the number of holes) is very small, since ion conduction has often a priority over electron conduction.

The oxygen partial pressure ($P_{O_2} \approx 0.2$) of the air may vary depending on the kind of oxide and corresponds to one of the regions A, B and C. When the oxygen partial pressure is within the range A, an oxide is called an n-type semiconductor. When the oxygen partial pressure is within the range C, an oxide is called a p-type semiconductor. Further, when the oxygen partial pressure is within the range B, an oxide is called an ionic conductor. In general, if a p-type semiconductor is used as an oxygen sensor, its conductivity is first lowered and then increased when the excess air ratio $\lambda$ is changed from the "lean" mixture to the "rich" mixture. Referring to FIG. 9, the partial pressure is changed from the region C to the region A, thus obtaining a two-valued function. Therefore, the p-type semiconductor is not suitable as a sensor whose resistance is abruptly changed near excess air ratio $\lambda = 1$. Further, most of the p-type semiconductors are very unstable in the "rich" mixture. However, an n-type semiconductor is very stable if the crystal structure is not changed. The n-type semiconductor stays in the region A even if the "lean" mixture is changed to the "rich" mixture. As a result, the conductivity simply increases, thus eliminating the drawback incurred in the p-type semiconductor.

If the conductivity greatly depends upon the oxygen partial pressure, the sensor is very sensitive to the gas. The dependency of the conductivity upon the oxygen partial pressure is generally given by the following relation in the region A or C:

$$\sigma \propto P_{O_2}{}^n \tag{1}$$

(for the n-type semiconductor as $n<0$, and the p-type semiconductor as $n>0$.)
If the absolute value of the exponent n is great, the sensor's sensitivity is improved. The exponent n is determined by the degree to which the lattice defects such as oxygen atom holes and metal atom holes are ionized. A few typical examples are illustrated below:

(EXAMPLE 1)

For charging the oxygen atom hole to be a monad, the exponent n is given as $-\frac{1}{4}$. The reaction formula in this case is given below:

$$O_o \rightleftarrows V_{\ddot{o}} + e' + O_2/2 \tag{2}$$

The above reaction formula indicates that, after the oxygen atom Oo in the oxygen lattice point is converted to the oxygen gas $O_2$, the conduction electrode e' and the oxygen atom hole $V_{\ddot{o}}$ which is ionized to be a monad are produced. The relation between the concentration of oxygen atom hole $[V_{\ddot{o}}]$, the conduction electron concentration $[e']$, and the oxygen partial pressure $P_{O_2}$ is established as follows:

$$[V_o][e']P_{O_2}{}^{\frac{1}{2}} = K_{V_o^{\bullet}} \tag{3}$$

where $K_{V_o}$ is the equilibrium constant of the reaction. Further, according to the law of conservation of electrical energy, the relation $[V_o] = [e']$ is given. Therefore, $$[e'] = K_{V_o^{\bullet}}{}^{\frac{1}{2}} P_{O_2}{}^{-\frac{1}{4}} \tag{4}$$

Since the conductivity $\sigma$ is proportional to the number of conduction electrons, the following relation is given:

$$\sigma \propto [e'] \propto P_{O_2}{}^{-1/4} \tag{5}$$

In this case, $n = -\frac{1}{4}$ is given.

(EXAMPLE 2)

For changing the oxygen atom hole to be a divalent ion, the exponent n is given as $-1/6$.
In this case, the following reaction formula is given:

$$O_o = V_{\ddot{o}} + 2e' + O_2/2 \tag{6}$$

where $V_{\ddot{o}}$ is a divalent-ionized oxygen atom hole. An equilibrium constant $K_{V_{\ddot{o}}}$ of the above reaction is given by the following relation:

$$[V_{\ddot{o}}][e']^2 P_{O_2}{}^{\frac{1}{2}} = K_{V_{\ddot{o}}} \tag{7}$$

Thus, according to the law of conservation of electrical energy, the relation $2[V_{\ddot{o}}] = [e']$ is given. Therefore, $$[e'] = (2K_{V_{\ddot{o}}})^{\frac{1}{3}} P_{O_2}{}^{-1/6} \tag{8}$$

and $$\sigma \propto P_{O_2}{}^{-1/6} \tag{9}$$

The exponent n is thus given as $-1/6$.

As described above, the exponent n varies depending upon the degree of ionization of the lattice defects. In general, the exponent is often determined to be a value between the above examples, that is, $1/6 < n < \frac{1}{4}$. Further, the exponent varies depending upon impurities contained in small amounts. Thus, even if the same oxide is used, the exponent may vary under different examining methods.

On the basis of various reference data, let us examine the patterns of dependency of conductivity upon the pressure of various oxides. An n-type semiconductor is used as a sensor which detects the excess air ratio $\lambda$ to be 1. In other words, in the sensor of this type, its resistance is greatly changed when the excess air ratio $\lambda$ is near 1. In this case, the exponent n is preferably great. Such a semiconductor material is $TiO_2$, $Nb_2O_5$, $Ta_2O_5$, $WO_3$ or $CeO_2$. However, if a sensor is used only in the "lean" mixture atmosphere, a p-type semiconductor may also be used. Therefore, CoO, NiO, $Y_2O_3$ or $HfO_2$ may be used as the p-type semiconductor sensor.

Figure 10:
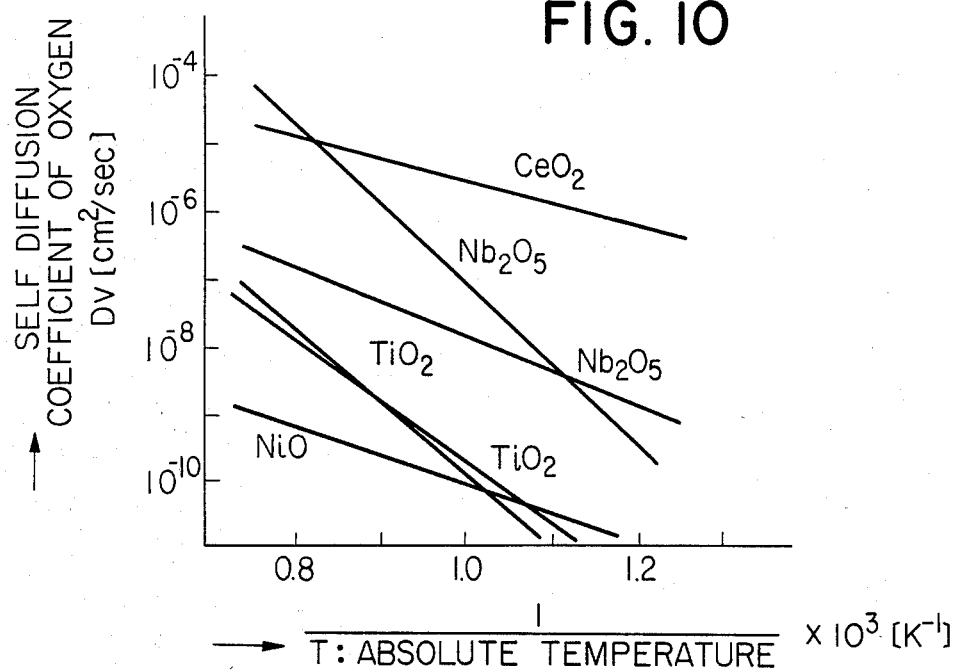
FIG. 10 is a graph showing the self diffusion rate of oxygen in various kinds of oxides as a function of temperature change.

The response time of the sensor will be described below. It is, of course, desirable that the sensor has a fast response time to the gas to be detected. The resistance of the oxide is greatly changed when its film thickness is thin. Further, the resistance changes quickly when the self diffusion coefficient of oxygen in the oxide is high. The present inventors searched from reference data for a material with a high self diffusion coefficient of oxygen. Results are shown in FIG. 10.

As is seen from the figure, the self diffusion coefficient of $CeO_2$ is the highest among the materials tested.

$Nb_2O_5$ has the next highest rate. The rates of $TiO_2$ and NiO are low.

Table 4 shows the relationship of response time between a thin film type sensor prepared by the sputtering method and a bulk type sensor prepared by the sintering method. The response time corresponds to a 50% logarithmic change in resistance. As may be seen from Table 4, a $Nb_2O_5$ film of 400 [Å] thickness has the fastest response time. The response time of a $CeO_2$ film of 500 [Å] thickness is close to that of the $Nb_2O_5$ film. Compared with the $Nb_2O_5$ film, the response time of the bulk type sensor is very long. However, if the film thickness is decreased, response time of the sensor of this type is greatly improved. However, as far as the $TiO_2$ film is concerned, slight improvement may be noticed, but no significant improvement can be found.

TABLE 4

Response Time for 50% Change in Sensor Resistance when "Rich" Mixture is Changed to "Lean" Mixture and Vice Versa

| Sample | Response Time When "Rich" Mixture is Changed to "Lean" Mixture [m sec] | Response Time When "Lean" Mixture is Changed to "Rich" Mixture [m sec] | Evaluation |
|---|---|---|---|
| $Nb_2O_5$ Thin Film Thickness: 400 [Å] | 73 | 29 | Excellent |
| $TiO_2$ Thin Film Thickness: 450 [Å] | 109 | 79 | Good |
| $TiO_2$ Sintered Body | 130 | 78 | Fair |
| $CeO_2$ Thin Film Thickness: 500 [Å] | 80 | 35 | Excellent |
| $Nb_2O_5$ Sintered Body | 600 | 153 | Fair |

As is apparent from the above table, the $Nb_2O_5$ and $CeO_2$ films are suitable materials for greatly improving the response time of the sensors.

Figure 11:
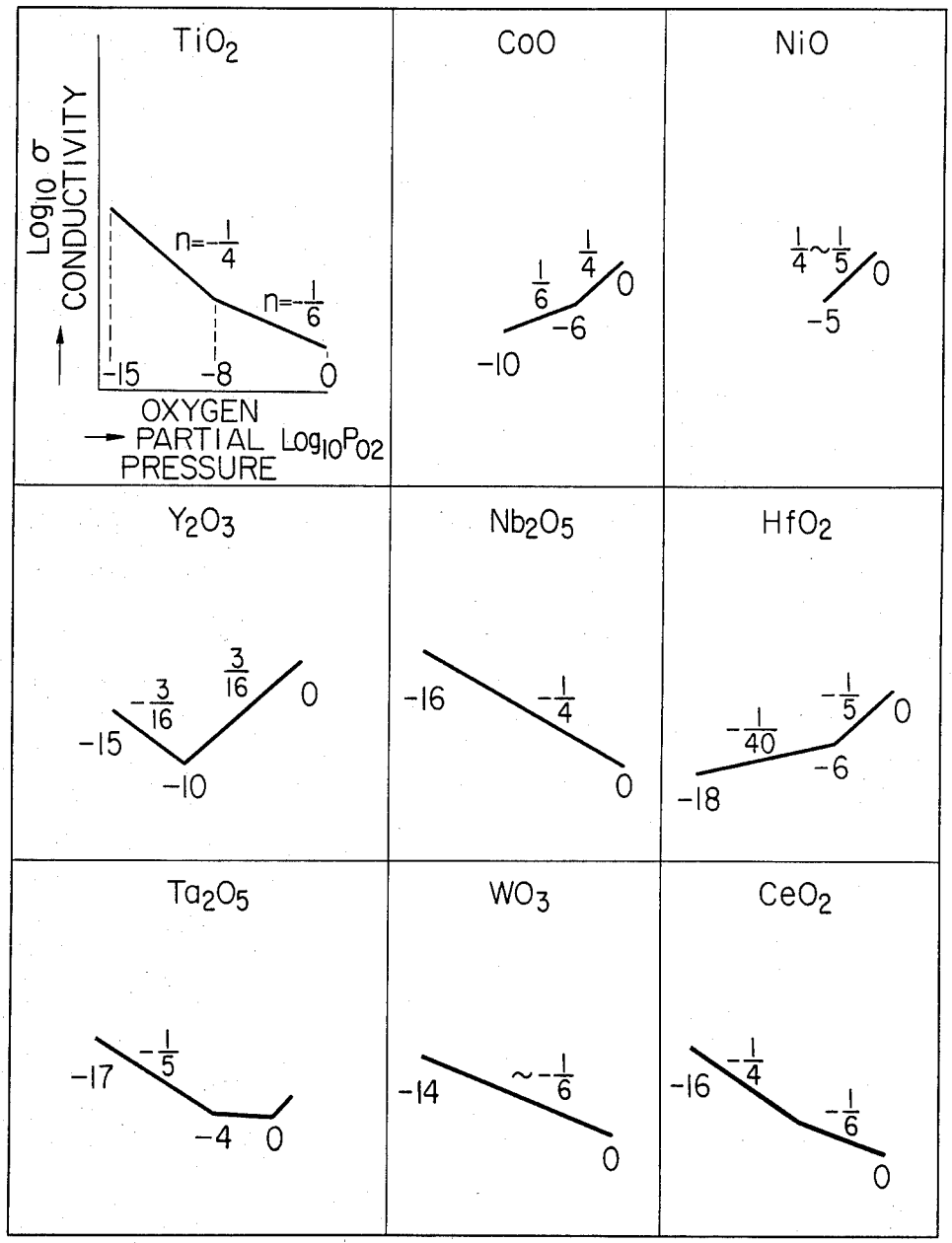
FIG. 11 shows graphs respectively showing conductivity as a function of an oxygen partial pressure in nine kinds of protective oxide semiconductors.

The range of resistance change will now be described below. It is desirable to use as a sensor for detecting the excess air ratio $\lambda = 1$, a material having a wide range of resistance change in the "rich" and "lean" mixture atmospheres. For this reason, the absolute value of the exponent n must be great. FIG. 11 shows the relationship between the oxygen partial pressure and the exponent in various oxides. As is apparent from the figure, the resistance of materials $TiO_2$, $Nb_2O_5$, $WO_3$ and $CeO_2$ respectively is a one-valued function when log $Po_2$ is in the range of 0 to $-14$, and has a large absolute value of the exponent.

The resistance will also be considered with respect to the temperature coefficient of resistance. The temperature coefficient of resistance in either one or in both of the "rich" and "lean" mixtures must be small to allow easy application of the sensor.

Figure 12A:
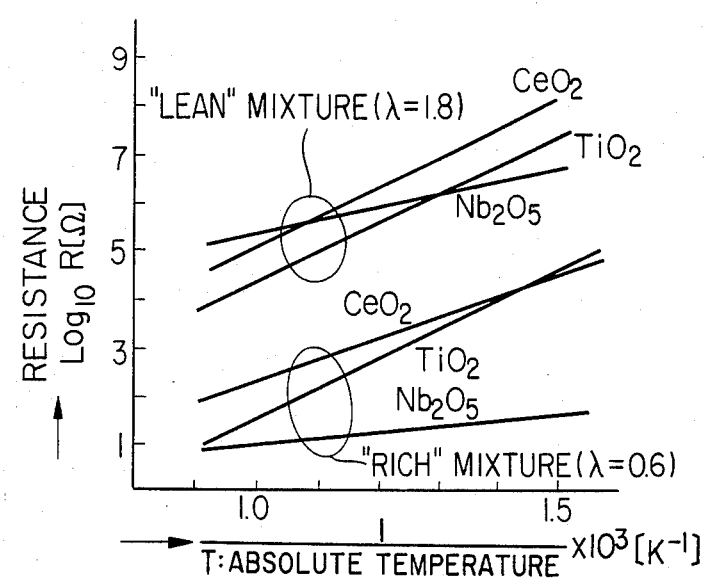
FIG. 12A is a graph showing resistance in $Nb_2O_5$, $CeO_2$ and $TiO_2$ as a function of a temperature.

FIG. 12A shows the relation between resistance and temperature in $Nb_2O_5$, $CeO_2$ and $TiO_2$ respectively.

Figure 12B:
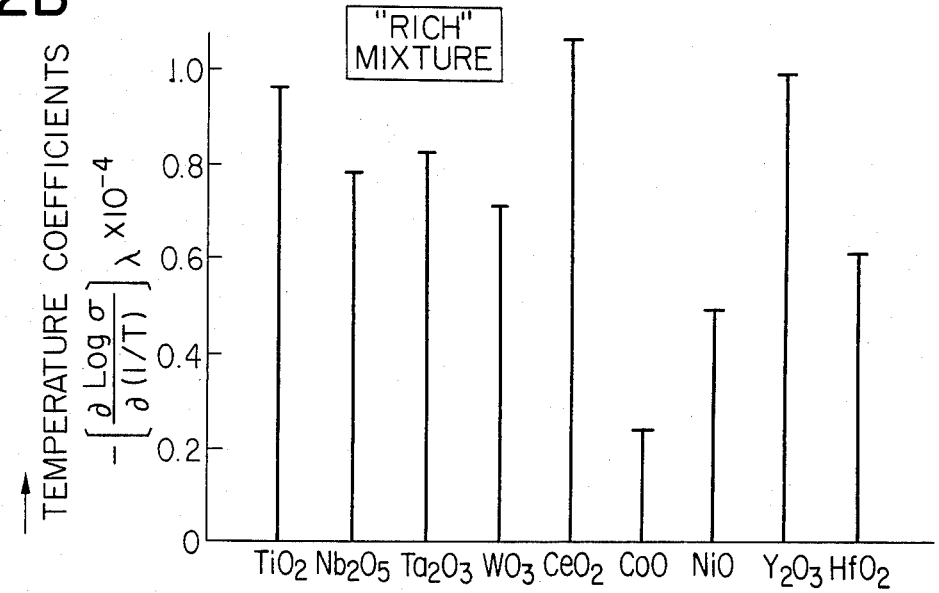
FIGS. 12B and 12C are respectively bar graphs showing conductivity in various kinds of oxide semiconductors as a function of a temperature coefficient.
Figure 12C:
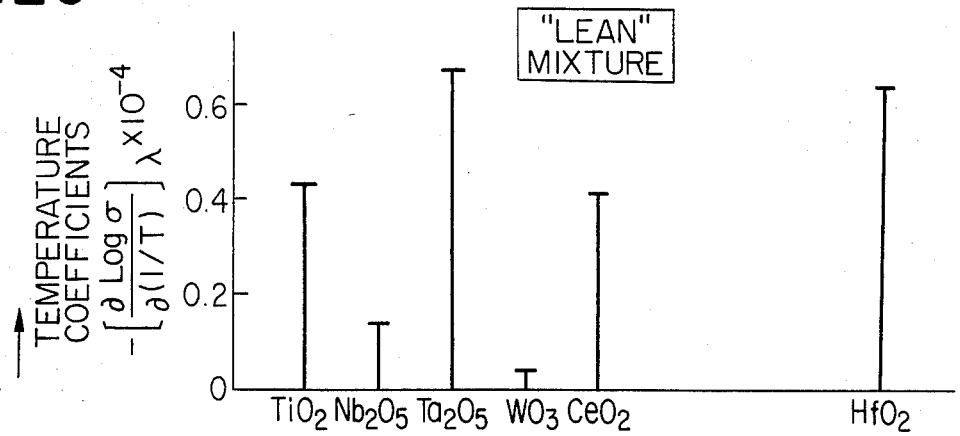
Figure 13:
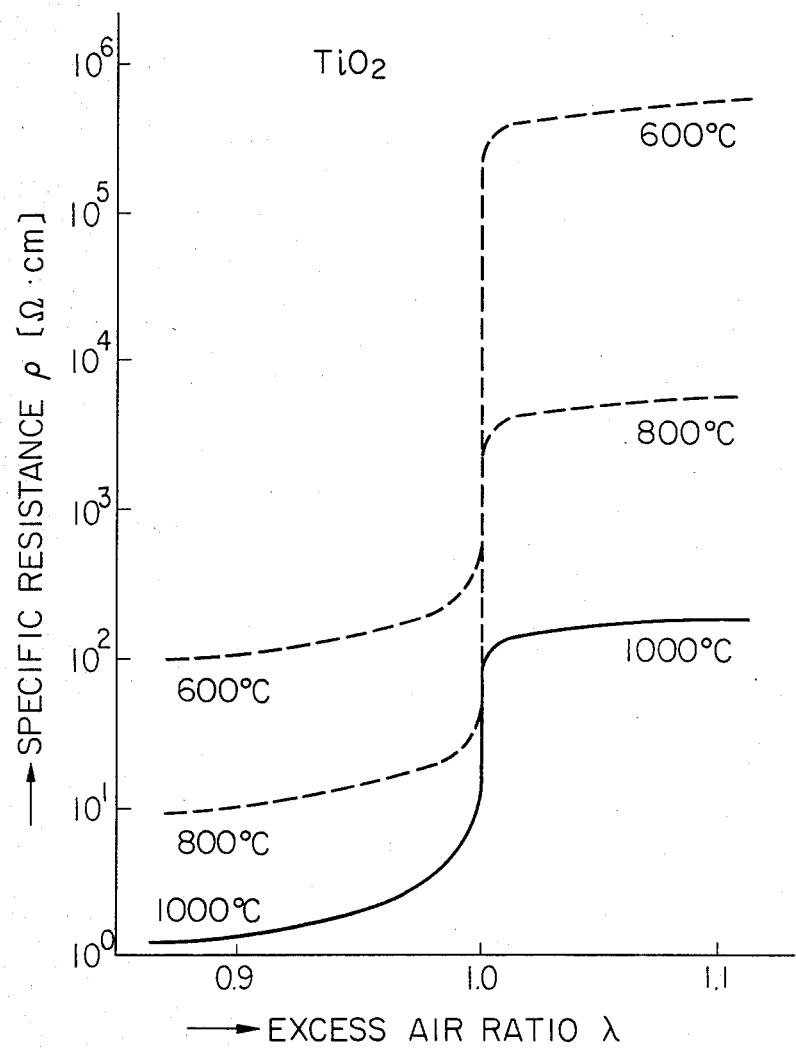
FIGS. 13 to 18 are graphs respectively showing specific resistance as a function of an excess air ratio in $TiO_2$, $Nb_2O_5$, $CeO_2$, $CoO$, $NiO$, and $HfO_2$.
Figure 14:
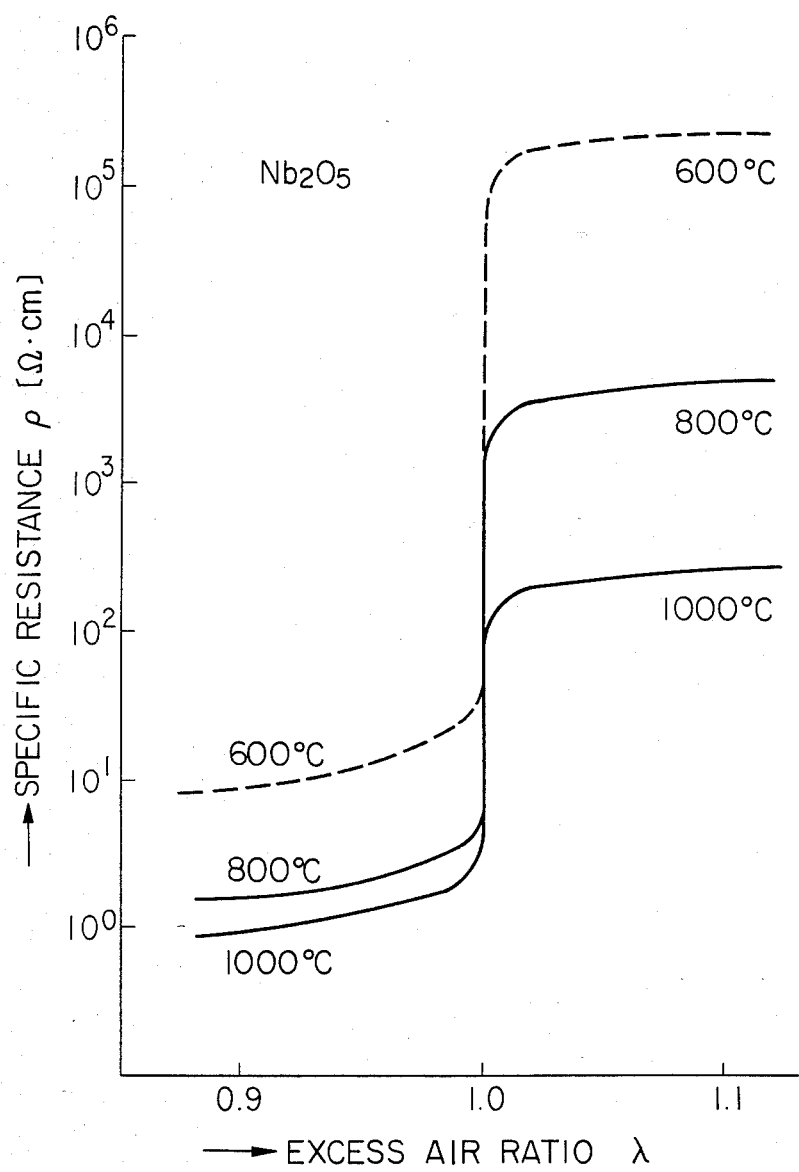
Figure 15:
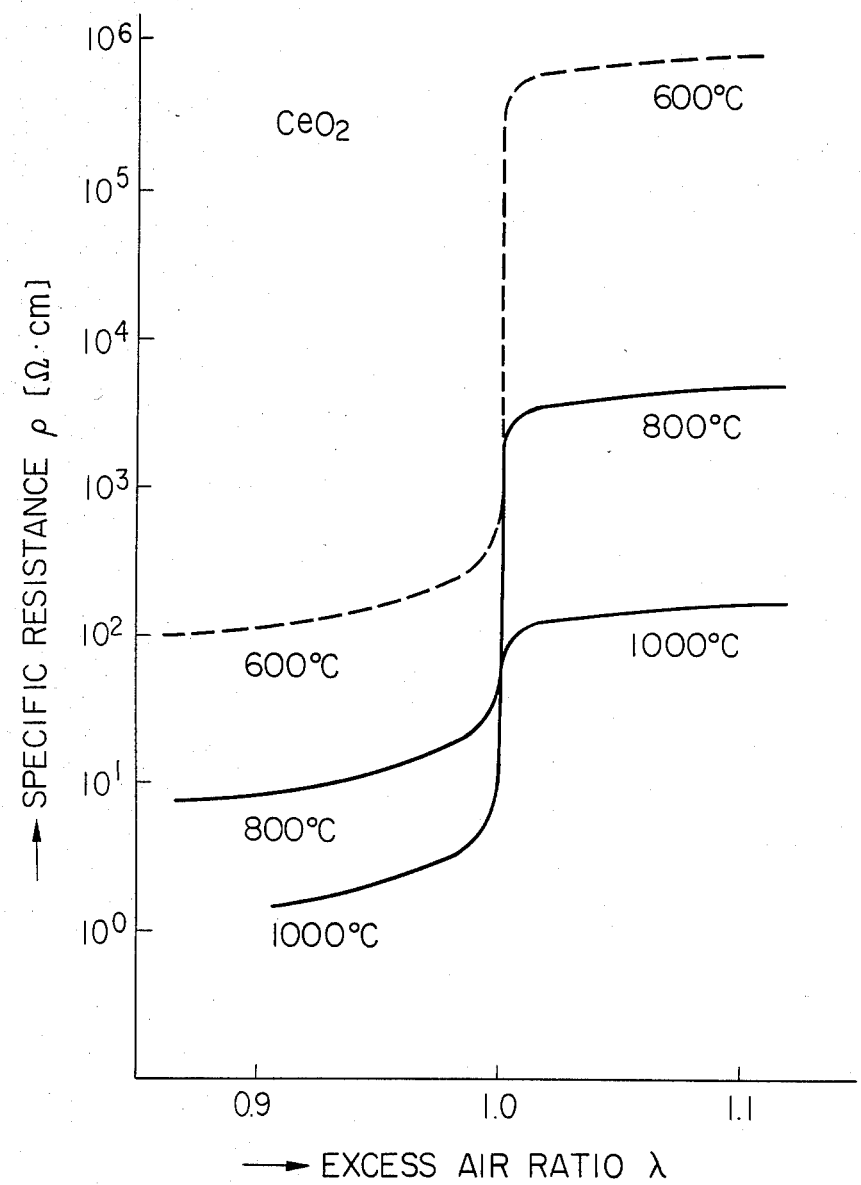
Figure 16:
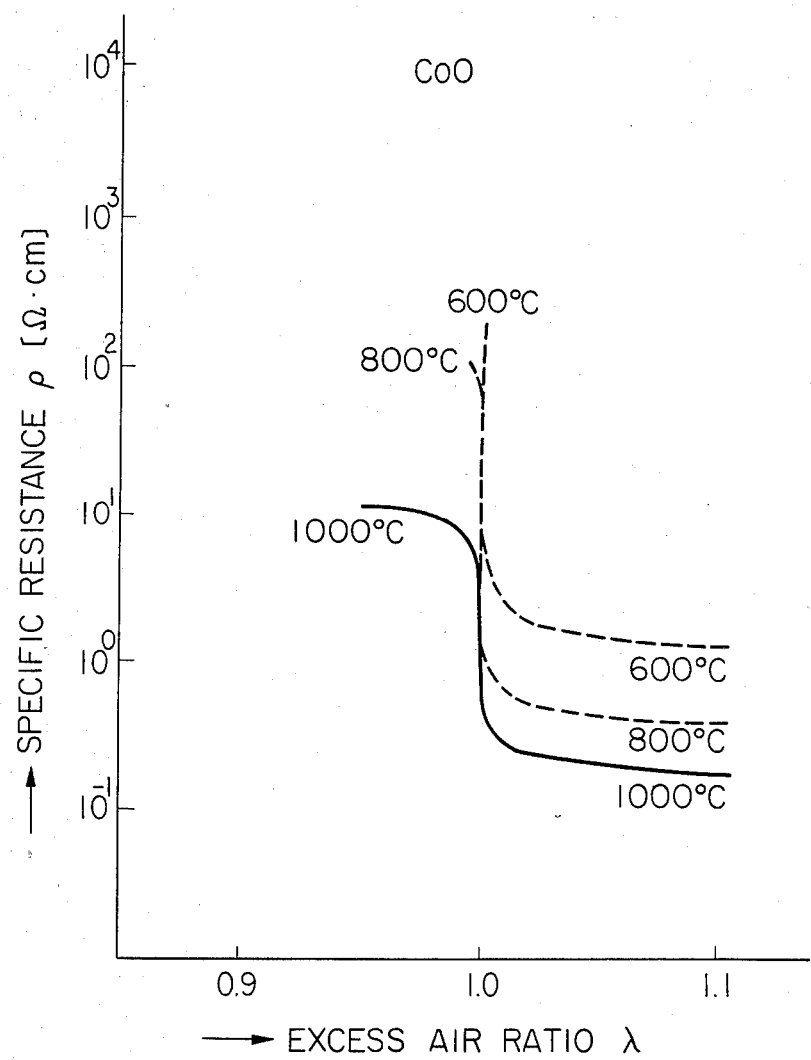
Figure 17:
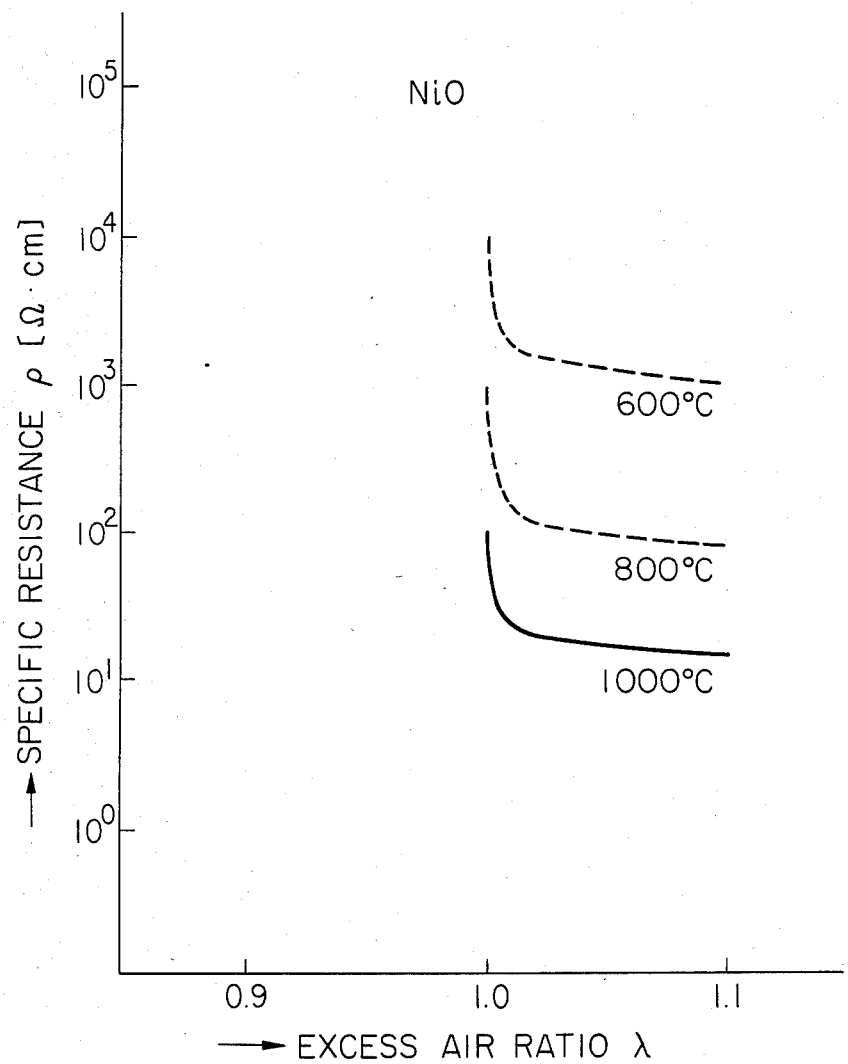
Figure 18:
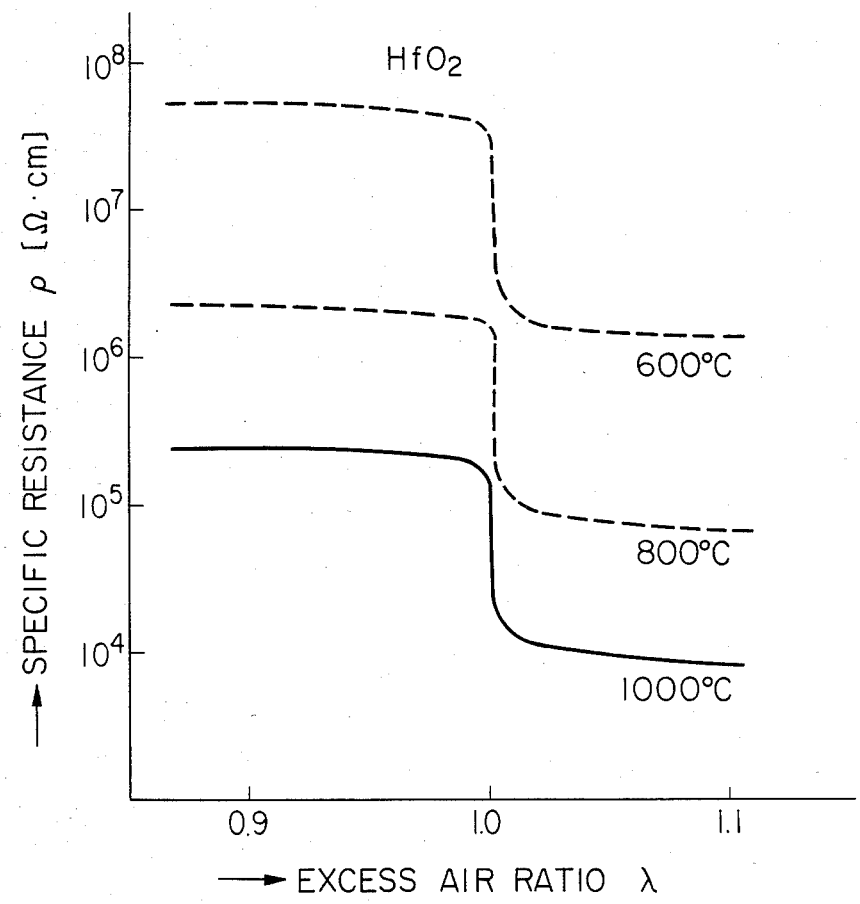

FIGS. 12B and 12C show respectively the temperature coefficients of conductivities of the oxide semiconductors. As is apparent from the figures, there is no material whose temperature coefficients in both the "rich" and "lean" mixtures is low. However, $WO_3$ and $Nb_2O_5$ have respectively low temperature coefficients in the "rich" mixture atmosphere.

FIGS. 13 to 18 respectively show the relationships between specific resistances ρ and the excess air ratio λ in $TiO_2$, $Nb_2O_5$, $CeO_2$, CoO, NiO and $HfO_2$. As is apparent from the figures, $TiO_2$, $Nb_2O_5$, $CeO_2$ and $HfO_2$ respectively have one-valued functions when the excess air ratio λ is in a range of 0.87 to 1.11 and may be operated stably. Among the above materials, specific resistances ρ of $TiO_2$, $Nb_2O_5$ and $CeO_2$ are low. However, $HfO_2$ has a high specific resistance and may not be formed as a thin film. Since the temperature coefficients of $TiO_2$ and $CeO_2$ are great, it is impossible to control the air-fuel mixture with a reference resistance at a temperature of 600 [°C.] to 1,000 [°C.]. However, since $Nb_2O_5$ has a small temperature coefficient in the "rich" mixture, the air-fuel mixture can be controlled with the reference resistance. CoO and NiO each have a small range of air-fuel ratio in order to perform stable operation. Finally, $WO_3$ is vaporized, resulting in inconvenience.

The above characteristics are summarized in Table 5. As is apparent from the table, $Nb_2O_5$ and $CeO_2$ are evaluated to be the best overall materials. $TiO_2$ is evaluated as fair, but no other material may be used as the sensor.

TABLE 5

| Characteristics | Oxide | | | | | | | | |
|---|---|---|---|---|---|---|---|---|---|
| | $TiO_2$ | $Nb_2O_5$ | $Ta_2O_5$ | $WO_3$ | $CeO_2$ | CoO | NiO | $Y_2O_3$ | $HfO_2$ |
| Applicable Range of Oxygen Partial Pressure | o | o | x | o | o | x | x | x | o |
| Responsiveness (Diffusion Rate) | Δ | o | | | | | x | | |
| Range of Resistance Change | o | ⊙ | | o | ⊚ | | | | Δ |
| Temperature Coefficient of Resistance | Δ | o | x | ⊙ | Δ | | | | x |
| Specific Resistance | o | o | | | o | | | | x |
| Vaporizability | o | o | o | x | o | o | o | o | o |
| Overall Evaluation | Δ | o | x | x | o | x | x | x | x |

⊙: Excellent
O: Good
Δ: Fair
x: Poor

The thickness of the thin film sensitive to oxygen is preferably in a range of 100 [Å] to 5 [μm] in consideration of its excellent response time to the gas, its stability, and resistance.

Any one of platinum (Pt), rhodium (Rh), palladium (Pd) and a mixture thereof is suitable as a reaction accelerating catalyst in consideration of the reaction acceleration effect and the stability.

Figure 19:
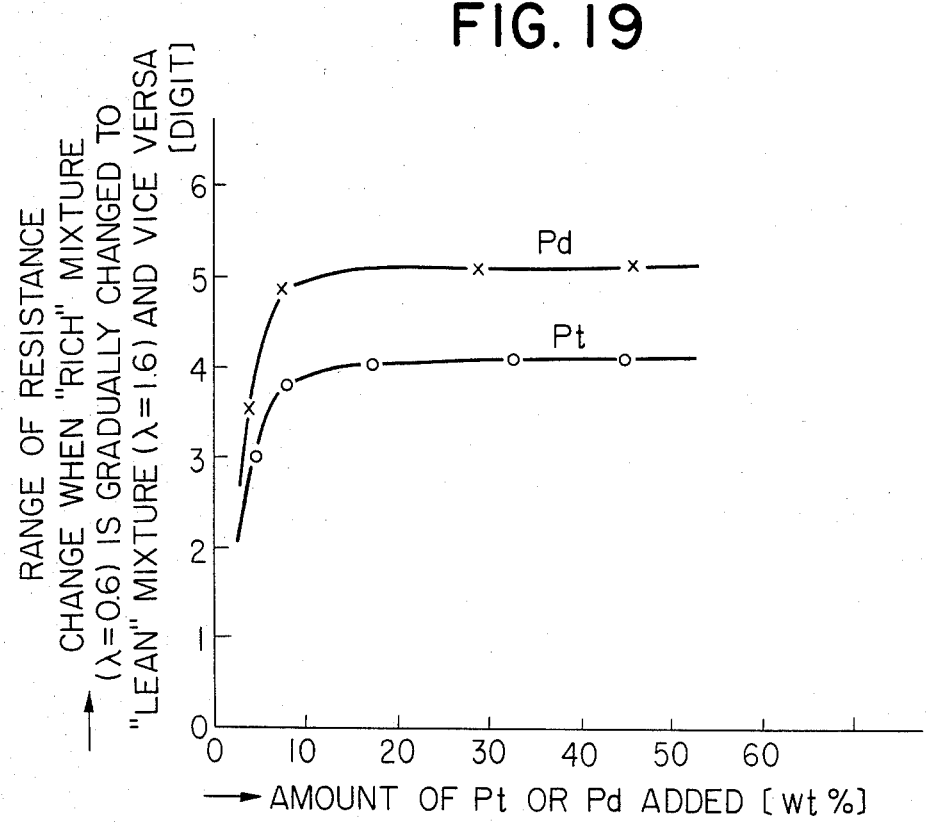
FIG. 19 is a graph showing the magnitude of change in a resistance as a function of an amount of Pt or Pd added, when the "rich" mixture is gradually changed to the "lean" mixture.

The amount of the catalyst to be added will be considered. FIG. 19 shows the relationship between the amount of the catalyst added and the range of resistance change when the "rich" mixture is changed to the "lean" mixture and vice versa. As is apparent from the figure, when the amount of Pt or Pd added is not less than 5 [wt %], a wide range of resistance change can be obtained, resulting in convenience. While the amount of Pt or Pd added is between 5 and 40 [wt %], the range of resistance changes is as wide as described above. However, when the amount is not less than 40 [wt %], the range is not widened further, but an apparent specific resistance is lowered. As a result, the amount to be added is preferably in the range of 5 [wt %] to 40 [wt %].

Figure 20:
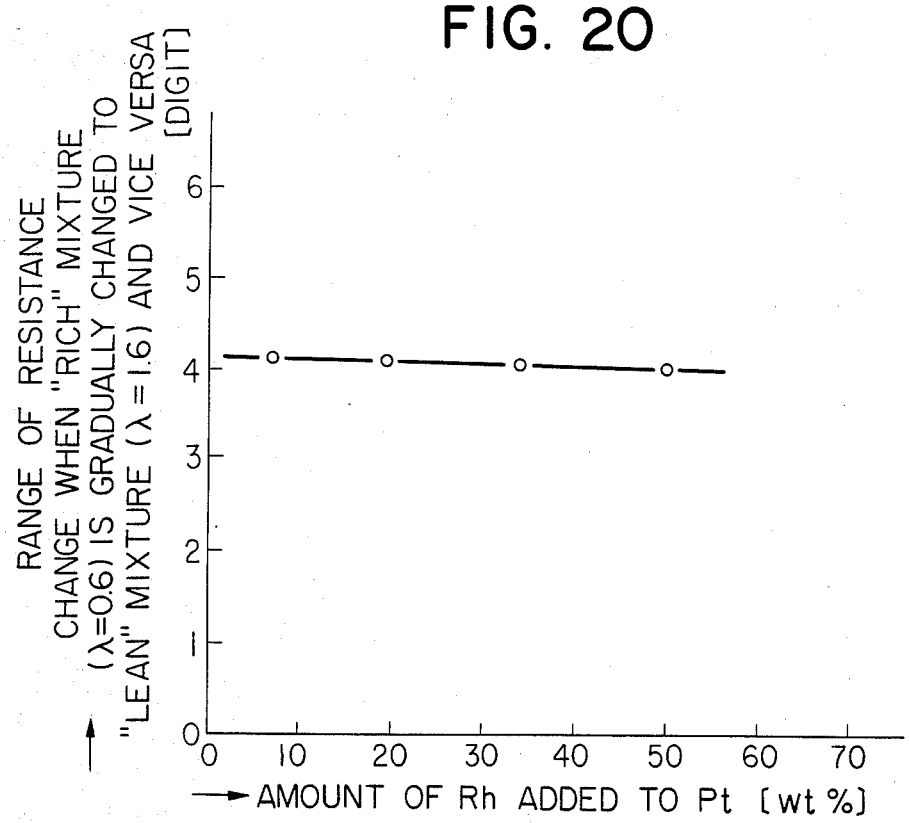
FIG. 20 is a graph showing the magnitude of change in a resistance as a function of an amount of Rh added to 20 [wt %] of Pt, when the "rich" mixture is gradually changed to the "lean" mixture.

FIG. 20 shows the relationship between the amount of Rh added to 20 [wt %] of Pt and the range of resistance change when the "rich" mixture is changed to the "lean" mixture and vice versa. As is apparent from the figure, even when Rh is added to Pt, the range of resistance change is not greatly changed. As a result, there is no advantage.

Any one of platinum (Pt), rhodium (Rh), palladium (Pd) and a mixture thereof is suitable as an electrode material formed on the thin film sensitive to oxygen in consideration of the stability and the temperature coefficient. The electrode preferably has a comb-shaped arrangement. The area of the opposing portions may then be increased, thus decreasing the resistance.

If a dense (nonporous) layer or porous layer is formed on the surfaces of the oxide and the electrodes, mechanical strength is improved and resistance to contamination is improved. Further, since supply of the combustible gas to the sensor is limited, the amount of heat produced in the reaction is then limited.

The thickness of the film varies depending on its density. Table 6 and FIG. 21 show the relationship between film thickness and response time when an $Al_2O_3$ dense thin film is sputtered onto the $Nb_2O_5$ thin film sensor.

TABLE 6

| Relationship Between Film Thickness and Response Time for 50% Change in Sensor Resistance when Excess Air Factor is changed from 0.95 to 1.05. | | | | | | |
|---|---|---|---|---|---|---|
| Film Thickness [Å] | 0 | 250 [Å] | 1050 [Å] | 2000 [Å] | 4000 [Å] | 7000 [Å] |
| Response Time | 82 [m sec] Exellent | 120 [m sec] Good | 260 [m sec] Fair | 600 [m sec] Fair | 3 min Poor | No Response Poor |

Figure 21:
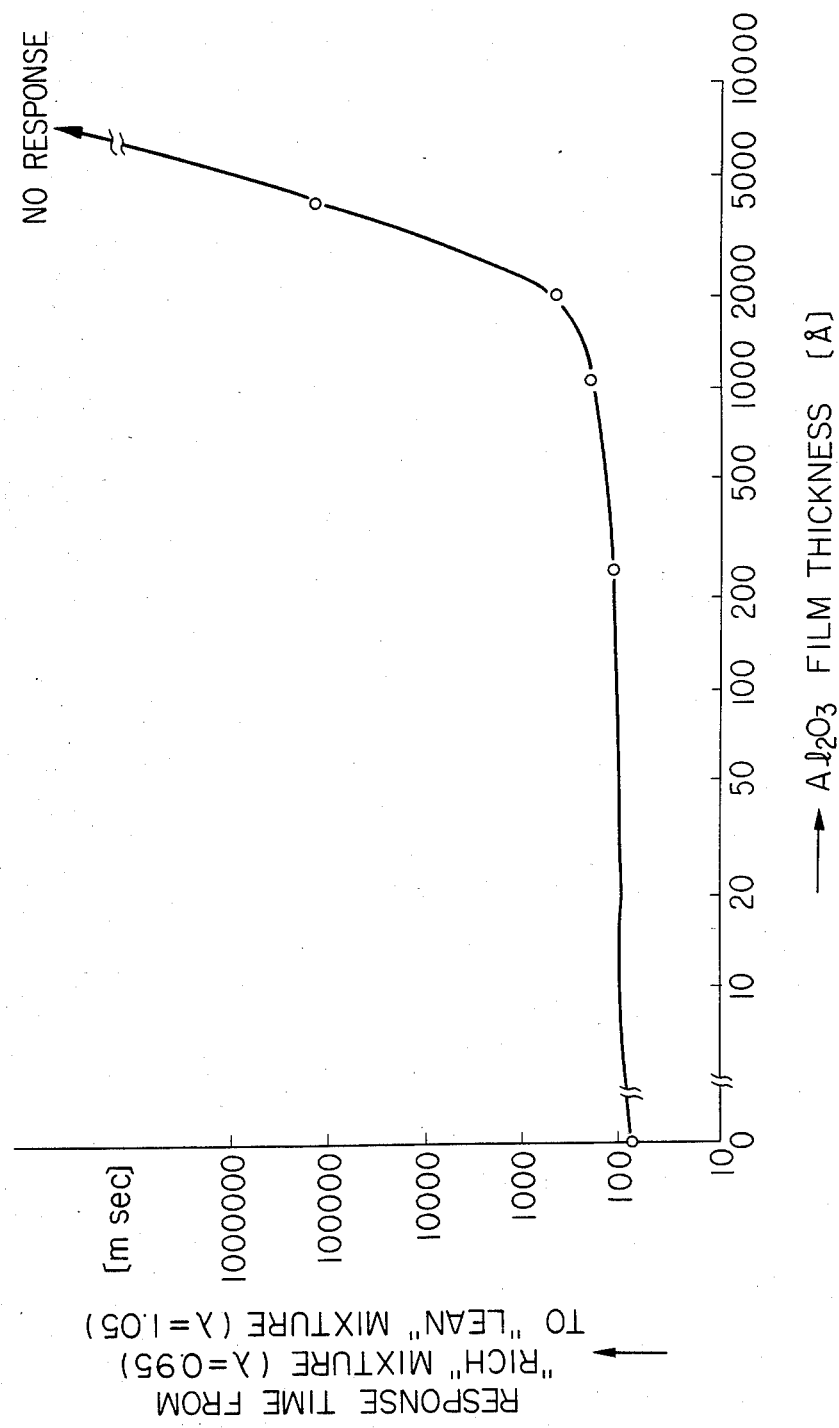
FIG. 21 is a graph showing response time from the "rich" mixture to the "lean" mixture as a function of a thickness of an $Al_2O_3$ film formed on the oxide semiconductor film by sputtering.

As is apparent from the Table 6 and FIG. 21, if the film thickness exceeds 2,000 [Å], the response time is extremely extended, resulting in inconvenience. The upper limit of the film thickness of the sputtered protective $Al_2O_3$ film is 2,000 [Å] to achieve the optimum response time.

A porous film may be coated as a protective film. A heat-resistant inorganic material such as a material based on silica, alumina, spinel, magnesia, or zirconia is suitable for the porous film. For forming a porous film by plasma-flame spraying a material based on spinel, an average particle diameter is 2 [μm] to 70 [μm]. The thickness of the porous film is preferably 20 [μm] to 300 [μm], so that peeling off and cracking are eliminated.

Figure 22:
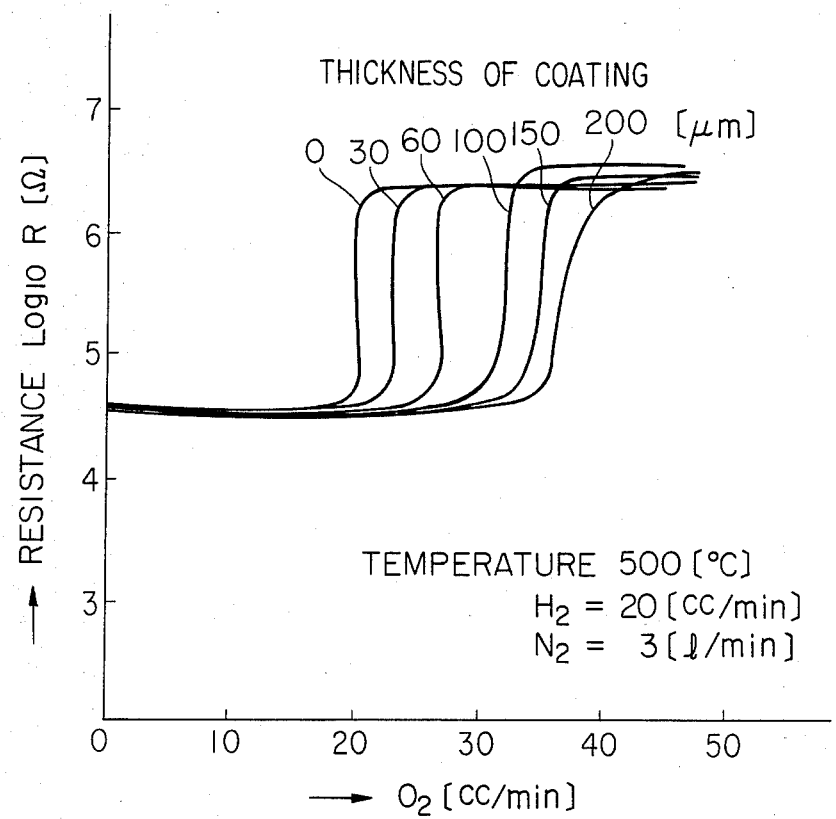
FIG. 22 is a graph showing resistance as a function of a gas composition in a porous spinel layer formed on the oxide semiconductor film by plasma flame spraying.

A coating was prepared by plasma flame spraying, using a material based on spinel with an average particle diameter of 20 [μm] to 70 [μm]. Thicknesses of the coatings were 0, 30, 60, 100, 150 and 200 [μm]. FIG. 22 shows the relationship between gas composition ($O_2$ concentration/$H_2$ concentration) and resistance. As is apparent from the figure, when the thickness of the coating is increased, a point where the resistance is abruptly changed is deviated greatly to the excess oxygen side. Further, it is found that the range of resistance change is narrowed. Although these characteristics correspond to a deviation in control of the air-fuel ratio when the material is used as an engine control sensor, the deviation may be corrected depending upon application. In this case, the thickness of the coating is preferably 20 [μm] to 300 [μm].

In the above description, the material based on alumina is used as the heat-resistant insulating substrate. For this purpose, materials based on silica, spinel, magnesia, or zirconia may also be used.

The present invention may also be practiced by forming a heater layer directly on a sensor (e.g., a limiting current type oxygen concentration sensor) which comprises an insulating substrate of another conductivity type, or by forming the heater layer indirectly thereon through a suitable insulating layer.

Further, the microheater according to the present invention can also be used as a contact combustion type gas sensor.

Further, the microheater can also be used for gas sensors except for an air-fuel ratio type sensor, and humidity sensors.

Further, a cylindrical heat-resistant insulating substrate may be used in place of a plate-shaped substrate.

The engine control sensor is mounted in a position where the flow rate of the gas and its temperature greatly vary. In general, when a temperature is changed, the sensor characteristics are also changed. In order to eliminate effects of the ambient temperature, a microheater is disposed on the sensor and a voltage applied thereto is controlled to maintain the heating temperature constant.

Figure 23:
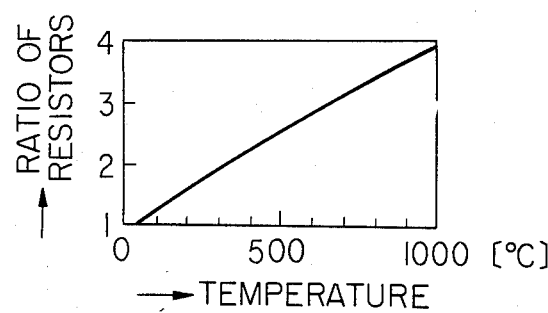
FIG. 23 is a graph showing characteristics of a platinum resistor as a function of temperature.

In order to maintain the temperature constant, a heat-sensitive element must be arranged to detect the temperature. If a platinum heater is used, the temperature coefficient of resistance of the heater is great (FIG. 23), so that the heater temperature can be obtained by the heater resistance, thus eliminating a separate heat-sensitive element. Thus, the sensor arrangement is simplified, resulting in low cost. Further, temperature detection is not delayed, so that no errors occur due to a temperature difference. In this case, since the heater is used as a heating means as well as a heat-sensitive element, a means must be provided to eliminate any interference between these two functions.

Figure 24:
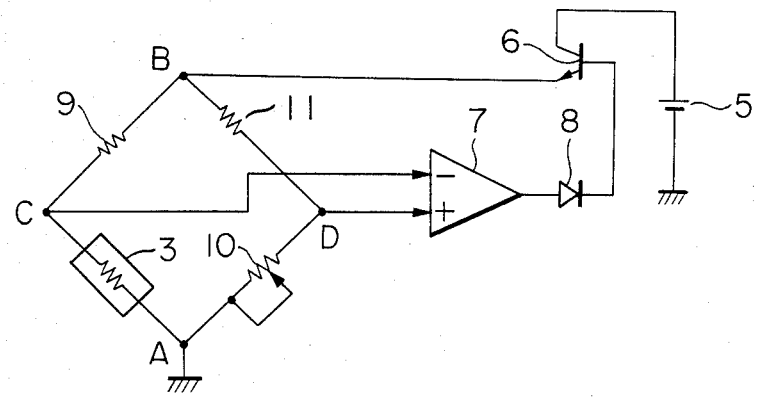
FIG. 24 is a circuit diagram of a constant temperature control circuit allowing heating of the oxygen sensor to a predetermined temperature.

FIG. 24 shows a constant temperature control circuit with a Wheatstone bridge for detecting a temperature by a resistance of the heater and for supplying power for heating. Referring to FIG. 24, the heater 3 is arranged between terminals C and A of the bridge. A voltage from a constant voltage source 5 is applied across terminals B and C of the bridge through a power control transistor 6. An unbalanced voltage across the terminals C and D of the bridge is detected and amplified by a differential amplifier 7 and is applied to the base of the power control transistor 6. In this circuit, a rectifying diode 8 is connected between the base of the power control transistor 6 and the output of the differential amplifier 7, so as to prevent a breakdown in the collector-base path. When the products of resistances of resistors at opposing sides of the bridge become equal, that is, when the product of the resistances of a resistor 9 and a potentiometer (variable resistor) 10 is equal to that of the resistances of a resistor 11 and the heater 3, the unbalanced voltage of the bridge becomes zero, so that constant power is applied across the heater 3 and the sensor temperature is kept constant.

Figure 25:
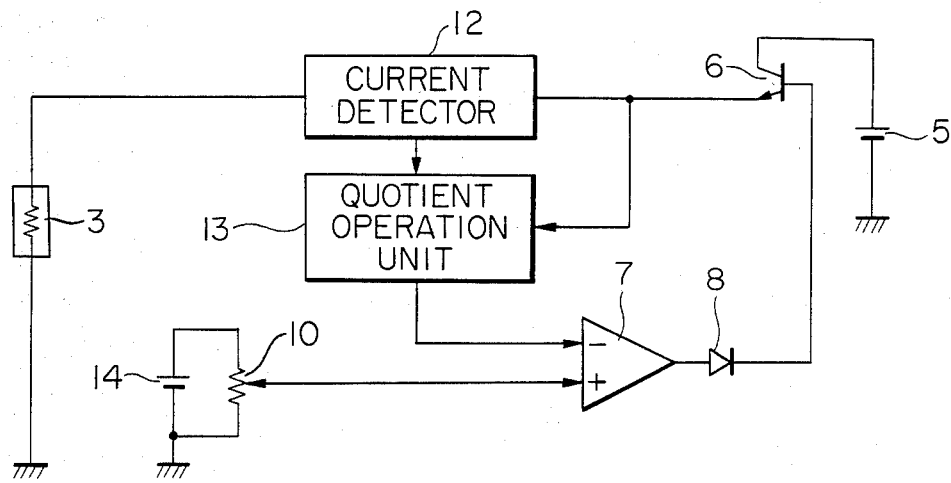
FIG. 25 is a block diagram showing another example of a constant temperature control circuit.

FIG. 25 shows another example of a constant temperature control circuit. A current detector 12 detects a current flowing through the heater 3. A quotient operation unit 13 detects a quotient V/I by dividing a heater voltage V by a detection current I. The quotient is proportional to the resistance of the heater 3. A voltage proportional to the reference resistance is set by the variable resistor 10 and is compared with the output voltage from the quotient operation unit 13. According to a differential output, the power control transistor 6 is controlled to make the sensor temperature constant.

Power may be continuously supplied to the heater whose temperature is to be kept constant. However, in order to decrease power loss and hence a rise in temperature, power may be intermittently supplied to the heater in accordance with a switching control method. In this case, the period is 1 [ms] to 100 [ms] in consideration of temperature stability.

Figure 26:
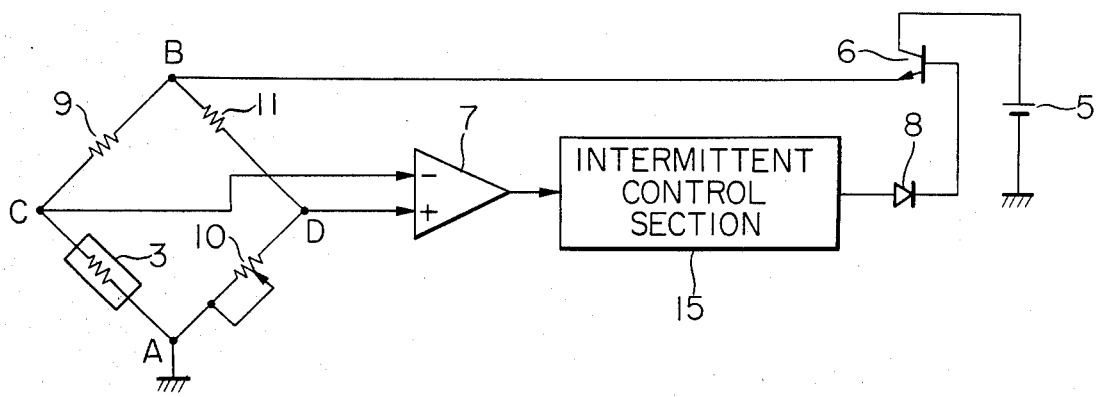
FIG. 26 is a block diagram of a constant temperature control circuit with an intermittent control section.

FIG. 26 shows still another example of a constant temperature control circuit for controlling power in accordance with the switching method. An intermittent control section 15 is arranged between the differential amplifier (measuring amplifier) 7 and the power control transistor 6.

Figure 27:
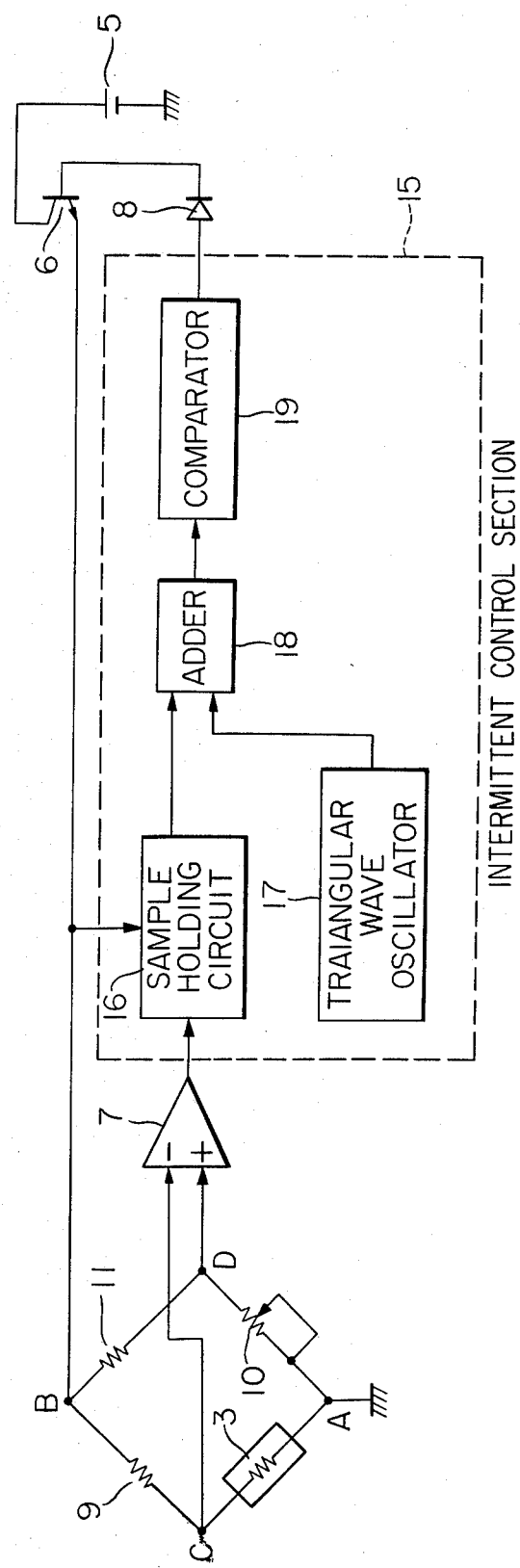
FIG. 27 is a detailed block diagram of the circuit shown in FIG. 26.

FIG. 27 is a detailed block diagram of the intermittent control section 15 shown in FIG. 26. In the switching method, an unbalanced voltage is obtained when the intermittent control section 15 is ON. However, if the section 15 is OFF, no unbalanced voltage is obtained. Therefore, the unbalanced voltage is held in a sample holding circuit 16. Meanwhile, a triangular wave oscillator 17 oscillates a triangular or similar voltage wave. An output from the sample holding circuit 16 and an output (voltage) from the triangular wave oscillator 17 are added by an adder 18. An output from the adder 18 is supplied to a comparator 19 and is shaped to be a rectangular wave with ON and OFF states. While the heater temperature is low, the ratio of ON time to OFF time is set to be high. However, when the heater temperature is high, the ratio of ON time to OFF time is set to be low. Thus, the sensor temperature can be kept constant. When the power control transistor is ON or OFF, only a small power loss occurs. Only in the switching or transient state from ON time to OFF time and vice versa does a relatively large power loss occur. As a result, average power loss is small and the resulting temperature rise due to the power loss slight is also small. The switching method described above is an excellent and very practical method when the heater is used on a vehicle and located near a high temperature of 130 [°C.], that is, when a high reliability is required and reliability of a transistor is degraded at a high temperature. The switching method may not be limited to ON time and OFF time. A two-state switching method for selectively switching high power and low power may also be utilized. According to this method, the unbalanced voltage is continuously applied, resulting in convenience.

Figure 28:
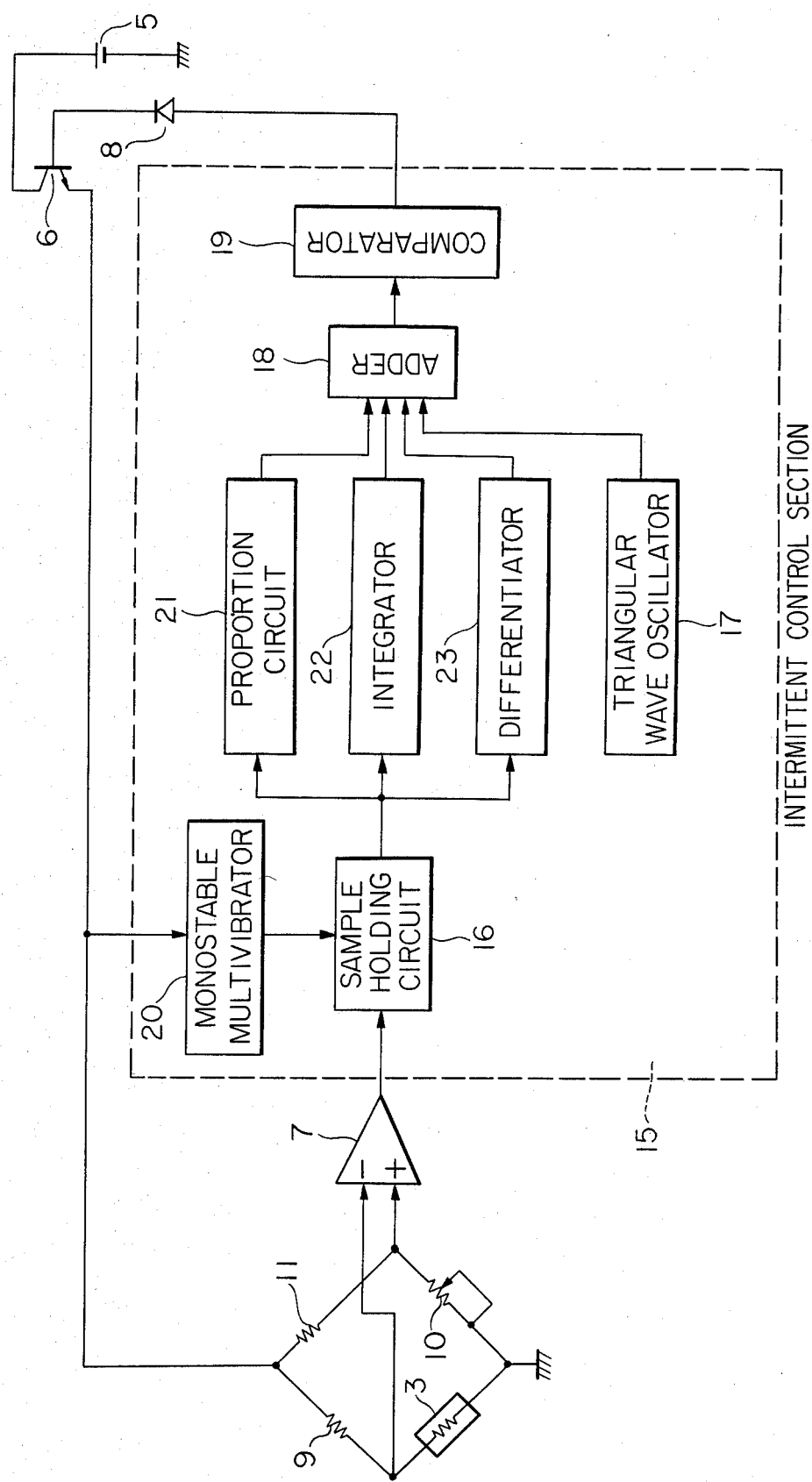
FIG. 28 is a block diagram showing another example of an intermittent control section.

FIG. 28 is another example of an intermittent control section 15. An output from the sample holding circuit 16 is supplied to a proportion circuit 21, an integrator 22 and a differentiator 23. Outputs from the proportion circuit 21, the integrator 22, the differentiator 23 and the triangular wave oscillator 17 are added by the adder 18 to perform stable control.

The intermittent control sections 15 shown in FIGS. 27 and 28 may be used in the constant temperature control circuit shown in FIG. 25 in the same manner.

Figure 29:
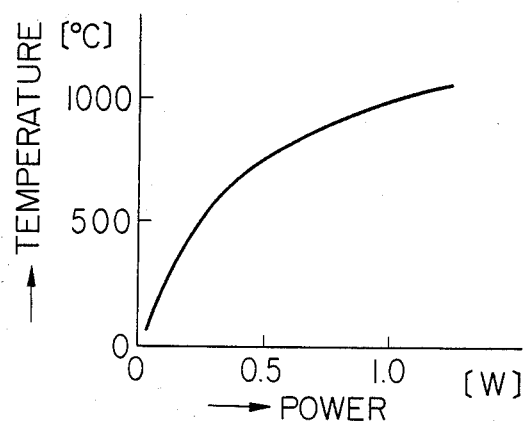
FIG. 29 is a graph for explaining the heater temperature as a function of input power.

FIG. 29 shows the relationship between the heater power and the temperature of the sensor shown in FIG. 1. Air flow rate is used as the parameter. As is apparent from the figure, a high temperature of 700 [°C.] can be obtained at input power of 0.5 [W].

Figure 30:
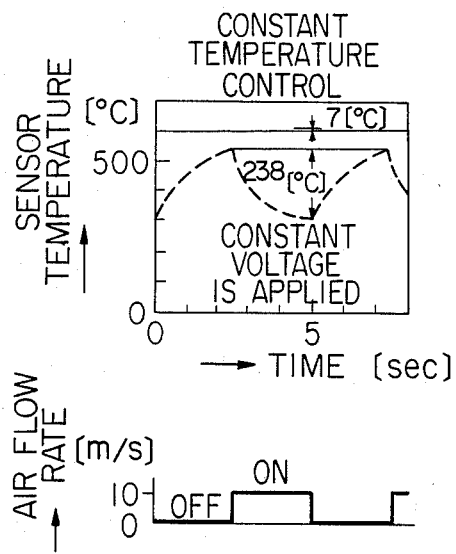
FIG. 30 is a graph showing the sensor temperature as a function of time in which a solid line indicates a result when constant heating control is performed under an air blowing condition and a dotted line indicates a result when constant heating control is not performed.

FIG. 30 shows temperature variation under the conditions in which the air flow rate is changed (0 [m/sec] and 10 [m/sec]). The solid line indicates the result when constant temperature control is performed. The temperature is only slightly changed by 7 [°C.] at the preset temperature of 600 [°C.]. However, the broken line indicates the result when a constant voltage is applied and constant temperature control is not performed. The temperature is greatly changed by 238 [°C.].

Figure 31:
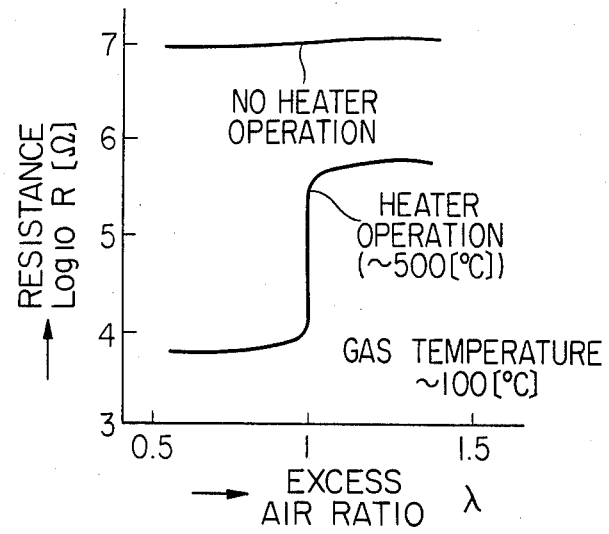
FIG. 31 is a graph showing the sensor resistance as a function of the excess air ratio when operation of the heater is used as a parameter.

FIG. 31 shows the relationship between the excess air ratio $\lambda$ and the logarithm of the resistance. As is apparent from the figure, when the ambient temperature (gas temperature) is as relatively low as 100 [°C.], niobium pentoxide ($Nb_2O_5$) is not substantially sensitive to the gas when it is heated by the heater. However, when it is heated by the heater to a temperature of 500 [°C.], its resistance is abruptly changed when the excess air ratio $\lambda$ is 1. Thus, niobirum pentoxide is effectively used as the sensor.

Figure 32:
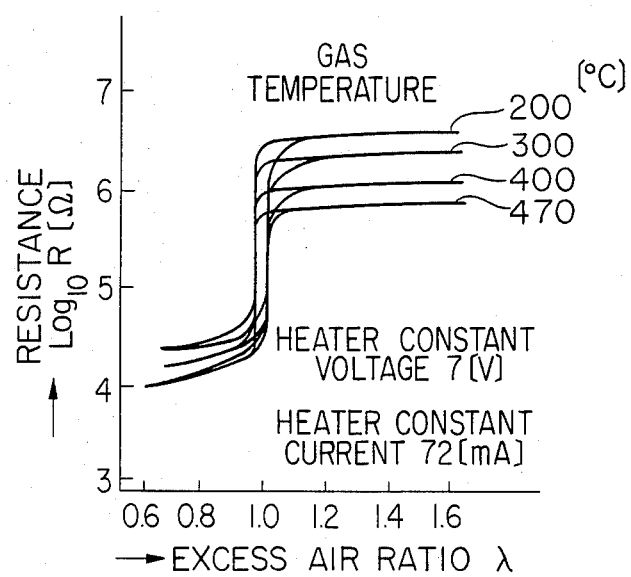
FIG. 32 is a graph showing resistance as a function of the excess air factor when the temperature of the exhaust gas is used as a parameter.

FIG. 32 shows the relationship between the logarithm of the resistance and the excess air ratio $\lambda$ when constant temperature control is not performed, when a constant voltage is applied and when the gas temperature is used as the parameter. As is apparent from the figure, only a slight adverse effect is obtained. Thus, a substantially satisfactory result is obtained.

FIG. 4 is a circuit diagram of the heater and the sensor when constant temperature control is not performed, and when a constant voltage is applied across the sensor.

Figure 33:
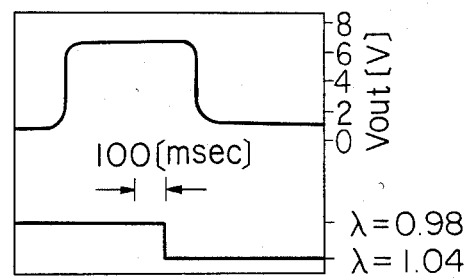
FIG. 33 shows an example of a response waveform in the circuit shown in FIG. 4.

FIG. 33 is an example of a "rich"-"lean" response waveform obtained in the circuit shown in FIG. 4 when the gas temperature is 100 [°C.], the heater temperature is 400 [°C.], and a signal of 1 [Hz] frequency is applied across the sensor. Since the sensor comprises a thin film, a fast response time is obtained.

Figure 34:
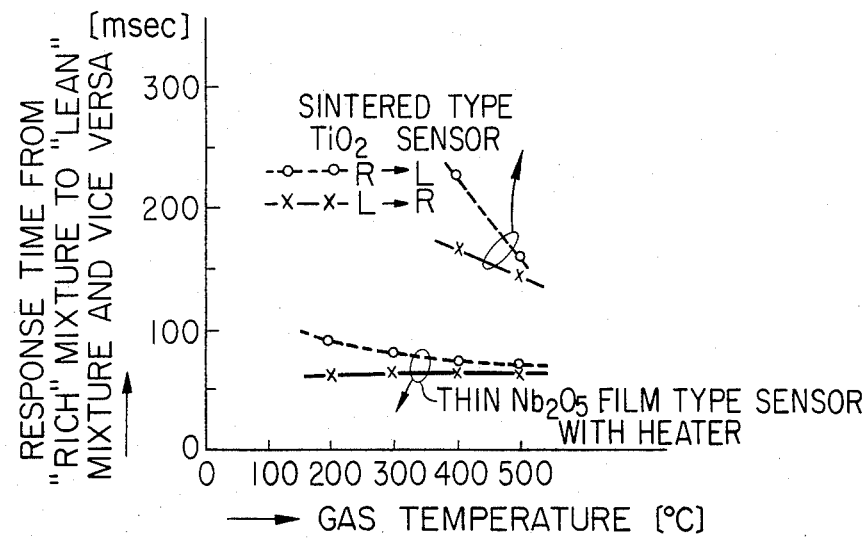
FIG. 34 is a graph for explaining the response time from the "rich" mixture to the "lean" mixture as a function of the gas temperature in a thin $Nb_2O_5$ film type sensor with the heater of the present invention and a sintered type $TiO_2$ sensor.

FIG. 34 shows the relationship between gas temperature and response time. The response time is long in the conventional sintered type $TiO_2$ sensor without a heater. Further, the gas temperature greatly influences the performance of the sensor. However, the response time is short in the thin film type $Nb_2O_5$ sensor with a heater. Further, the gas temperature only slightly influences the performance of the sensor.

Figure 35:
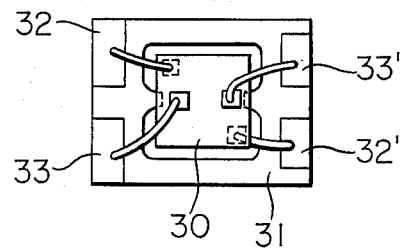
FIG. 35 is a plan view of a sensor with the microheater of the present invention on a base.
Figure 36:
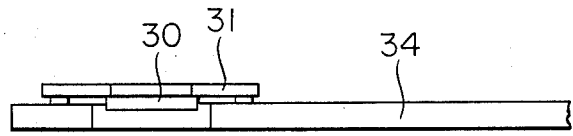
FIG. 36 is a side view of a holder on which a sensor-base assembly is mounted.
Figure 37:
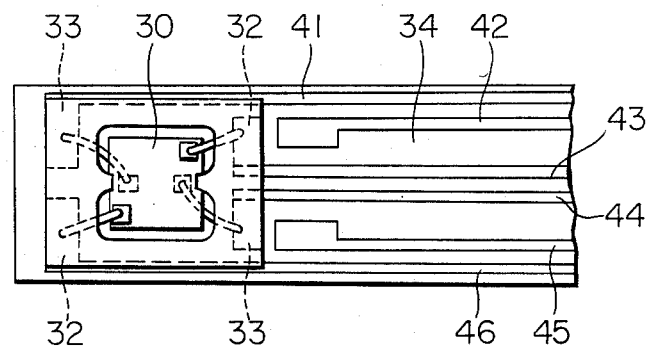
FIG. 37 is a plan view of the holder shown in FIG. 36.
Figure 38:
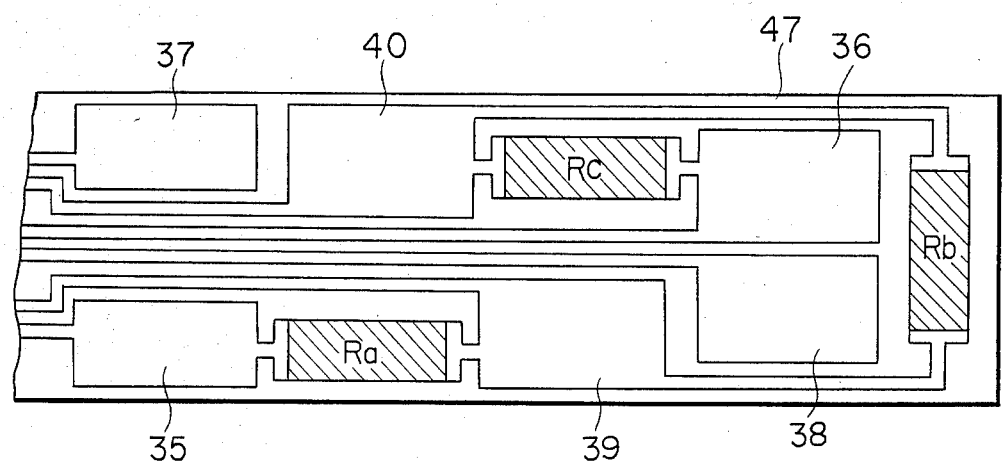
FIG. 38 is a plan view of proximal portion of the holder on which are terminals and resistors for a Wheatstone bridge.
Figure 39:
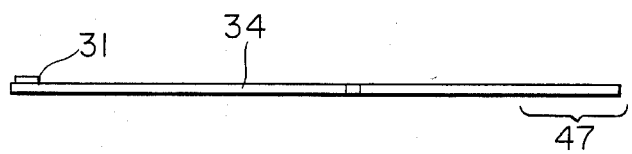
FIGS. 39 and 40 are respectively a side view and a plan view showing the outer appearance of the holder.
Figure 40:
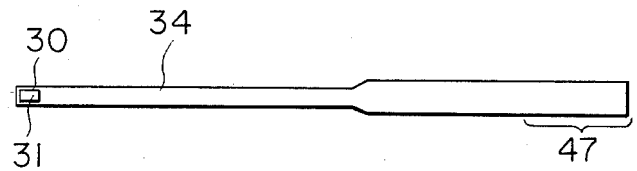

FIGS. 35 to 40 show an example of a holder for holding the oxygen sensor with a microheater according to the present invention. FIG. 35 is a plan view of a base which is mounted on a distal end of the holder. An oxygen sensor 30 is mounted at the center of a base 31. Electrodes 32 and 32' and electrodes 33 and 33' on the base 31 are respectively connected to the heater electrodes and the sensor electrodes of the sensor 30. FIG. 36 is a side view of the distal end of the holder, and FIG. 37 is a plan view thereof. FIG. 38 is a plan view of a proximal portion of the holder. Resistors Ra, Rb and Rc which constitute the Wheatstone bridge and electrodes for connections are arranged in a proximal portion 47 of a holder 34. The electrodes are connected to the distal end of the holder by means of Pt lead wires 41 to 46. The base 31 on which the oxygen sensor is mounted is electrically connected and fixed by platinum bonding at the distal end of the holder. FIGS. 39 and 40 are a side view and a plan view respectively showing the overall structure of the holder.

As is apparent from the above description in which the microheater according to the embodiment of the present invention is described and illustrated in detail, the oxygen sensor comprises a proper combination of a heat-resistant insulating substrate and a heater layer sputtered thereon so as not to cause a reaction between the substrate and the heater layer, thus providing a stable sensor. Further, the oxygen sensor according to the present invention can be used under abrupt cooling and heating conditions in a wide temperature range from ambient temperature to 800 [°C.]. Further, the oxygen sensor is coated with a surface layer of a proper material, so that the sensor is not damaged by combustible components, and has a resistance to corrosive gas, thus providing a long service life. Further, excellent workability is guaranteed and the sensor can be manufactured at low cost.

A limiting current type oxygen sensor according to another embodiment of the present invention will be described hereinafter.

Figure 41:
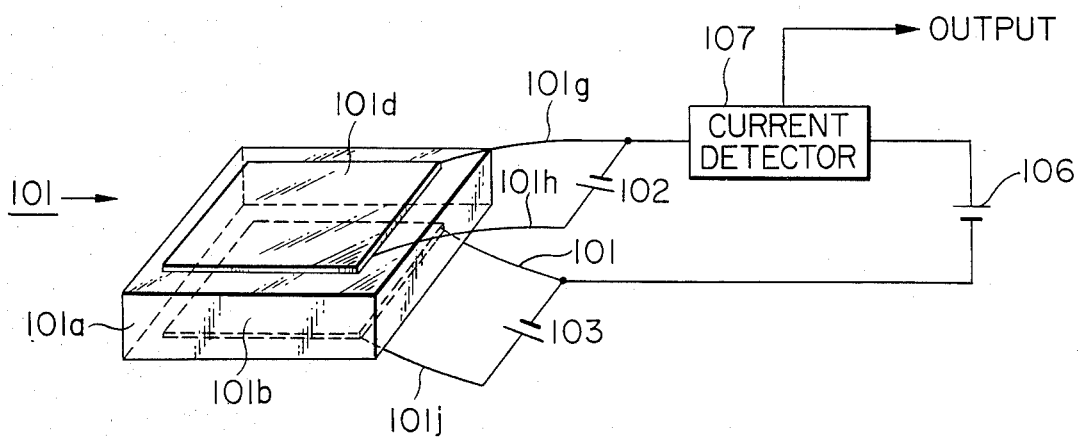
FIG. 41 shows an example of the arrangement of a limiting current type oxygen sensor according to the present invention and its connections with a constant voltage circuit and a limiting current measuring circuit.

Referring to FIG. 41, a cathode 101b is formed on one major surface of a plate 101a of an oxygen ionic conductor 101, and an anode 101d is formed on the other major surface thereof. Two lead wires 101j and 101i are connected to the cathode 101b, and two lead wires 101h and 101g are connected to the anode 101d. The cathode and anode 101b and 101d respectively function as the electrodes of the limiting current type oxygen sensor and also function as heaters for heating the sensor. A voltage from a power source 103 is applied to the cathode 101b through the lead wires 101i and 101j, so that the cathode 101b is heated. Similarly, a voltage from a power source 102 is applied to the anode 101d through the lead wires 101g and 101h, so that the anode 101d is heated. When the voltages are respectively applied to the cathode and anode 101b and 101d, a potential gradient of several volts up to about twenty volts is formed within the surfaces of the electrodes. If the same voltage is applied from the power sources 102 and 103 and the voltage applying direction is the same, the potential gradients become the same on the electrodes, so that no adverse effect of the voltage is seen between the cathode 101b and the anode 101d. For this purpose, the shapes, sizes and arangements of the cathode 101b and the anode 101d must be the same. In other words, the cathode 101b and the anode 101d must be symmetrical about a plane which is parallel to the surface on which the electrodes 101a and 101b are formed and which passes the center of the plate 101a of the oxygen ionic conductor. The lead wires 101g and 101gh must be symmetrically arranged with the lead wires 101i and 101j.

Figure 42:
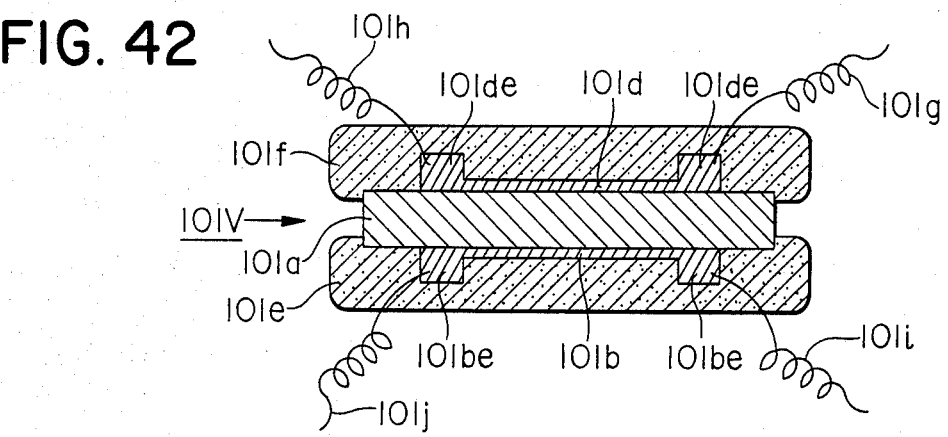
FIG. 42 shows a limiting current type oxygen sensor with a cathode/heater structure wherein portions thereof connected to the lead wires are made thick to decrease an electric resistance thereof.

In order to achieve a uniform density of a current flowing from the rectangular cathode 101b which also functions as a heater (to be referred to as a heater/cathode 101b hereinafter) and the rectangular anode 101d which also functions as a heater (to be referred to as a heater/anode 101d hereinafter), thick portions 101de and 101be are formed at the end portions of the heater/-cathode and heater/anode 101d and 101b, as shown in FIG. 42.

Figure 43:
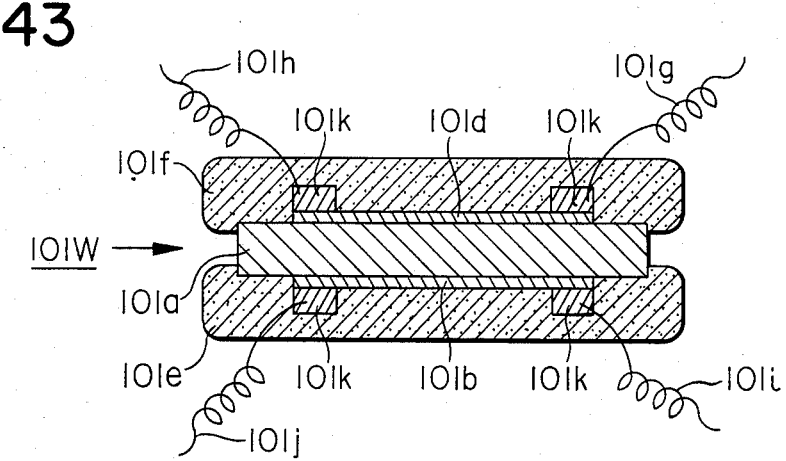
FIG. 43 shows a limiting current type oxygen sensor with a cathode/heater structure wherein portions thereof connected to the lead wires comprise a low resistant material to decrease an electric resistance thereof.
Figure 44:
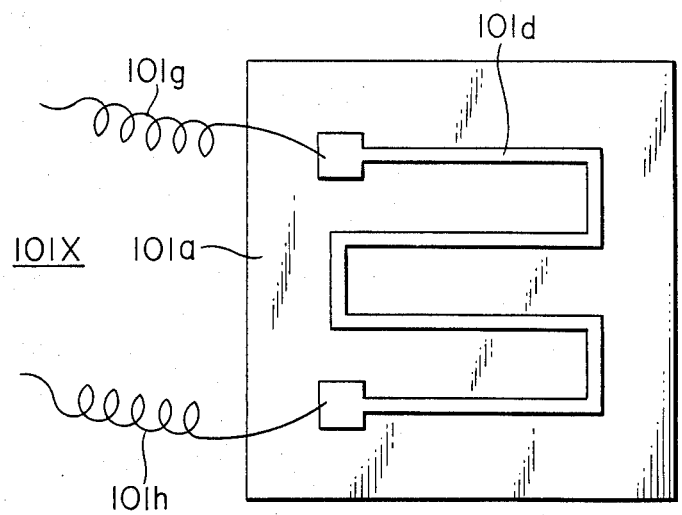
FIG. 44 shows a limiting current type oxygen sensor with a structure in which a band-shaped anode/heater or cathode/heater is shaped in a zigzag manner to increase the overall length thereof.

For the same purpose, members 101k which have a specific resistance smaller than that of the electrode material (heater material) may be disposed at the end portions of the heater/cathode 101b and the heater-/anode 101d, as shown in FIG. 43.

Figure 45A:
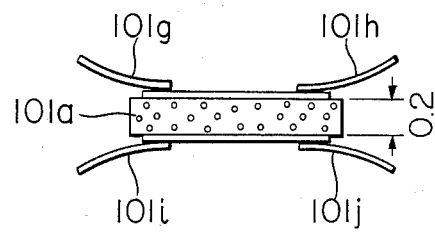
FIGS. 45A and 45B are a side view and a plan view respectively of a limiting current type oxygen sensor with a structure in which a band-shaped anode/heater or cathode/heater is shaped in a zigzag manner to increase the overall length thereof.
Figure 45B:
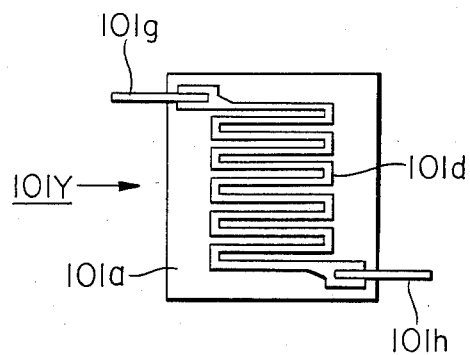

The cathode and anode have a rectangular shape as shown in FIG. 41. However, as shown in FIGS. 45A and 45B, they may be of a band shape. In this case, the heater/anode and heater/cathode must have the same shape and the same size, and must be disposed in corresponding positions on opposing major surfaces of the oxygen ionic conductor.

The material of the oxygen ionic conductor 101 is a material in which a stabilizer such as $Y_2O_3$, $GbO_3$, $Gd_2O_3$, $MgO$, $CaO$ or $Sc_2O_3$ is solid dissolved in zirconia, a material in which a stabilizer such as $Y_2O_3$, $Er_2O_3$ and $WO_3$ is solid dissolved in $Bi_2O_3$, or a dense sintered body in which a stabilizer such as $CaO$, $MgO$, $Y_2O_3$ and $Yb_2O_3$ is solid dissolved in $HfO_2$ or $ThO_2$.

A method for manufacturing the material for the heater/cathode and heater/anode is substantially the same as that for manufacturing the thin oxide film of the oxygen sensor in the first embodiment. A material is selected from one of platinum, rhodium, palladium and a mixture thereof. A manufacturing method is substantially the same as that shown in FIG. 2 except that an oxygen ionic conductor is used in place of the $Al_2O_3$ substrate.

The heater/cathode 101b is coated with a porous protective layer 101e which limits the flow rate of oxygen i.e. oxygen permeation flowing therein. Similarly, the heater/anode 101d is coated with a porous protective layer 101f (FIGS. 42 and 43).

Figure 46:
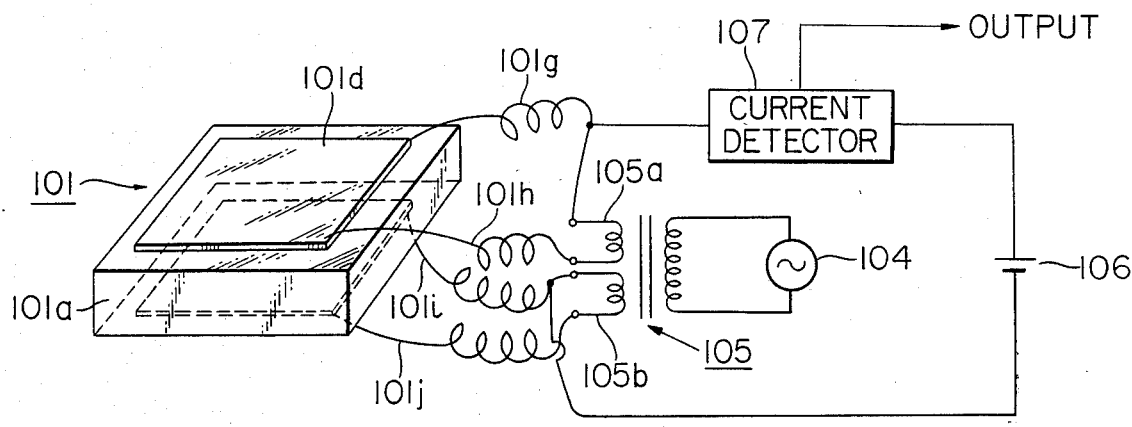
FIG. 46 shows an example of a control circuit for controlling the alternating current flowing through the cathode/heater and anode/heater.

The power sources 102 and 103 may supply a DC voltage as shown in FIG. 41. However, as shown in FIG. 46, they may also supply an AC voltage.

The mode of operation of the circuit shown in FIG. 41 will be described below.

A limiting current measuring DC voltage is applied across the heater/anode 101d and the heater/cathode 101b of the limiting current type oxygen sensor 101 from a power source 106. The limiting current is detected by a current detector 107.

A heating voltage is applied from the power source 103 to the heater/cathode 101b. A heating voltage is applied from the power source 102 to the heater/anode 101d. As described above, the potential profiles of the heater/cathode 101b and the heater/anode 101d are symmetrical. Therefore, no potential difference between the heater/cathode 101b and the heater/anode 101d due to heating voltages is found in the oxygen ionic conductor. Therefore, the potential difference between the heater/cathode 101b and the heater/anode 101d is substantially the same as a voltage of the power source 106, so that the electrodes are not influenced by the heater heating voltages, and the limiting current is highly accurately measured.

The ratio of output current $Il(T_0)$ at a temperature $T_0$ to the output current $Il(T)$ at a temperature $T$ under the same oxygen partial pressure is defined as a function $(Il(T)) (Il(T_0))$ of the output current on temperature and is given as follows:

$$(Il(T))/(Il(T_0)) = (T/T_0)^m$$

As is apparent from the above expression, if the measured temperature T varies, the limiting current Il(T) varies, resulting in an error. Since the exhaust gas temperature of the internal combustion engine generally varies, the temperature must be kept constant to measure the current at constant temperature.

Figure 47:
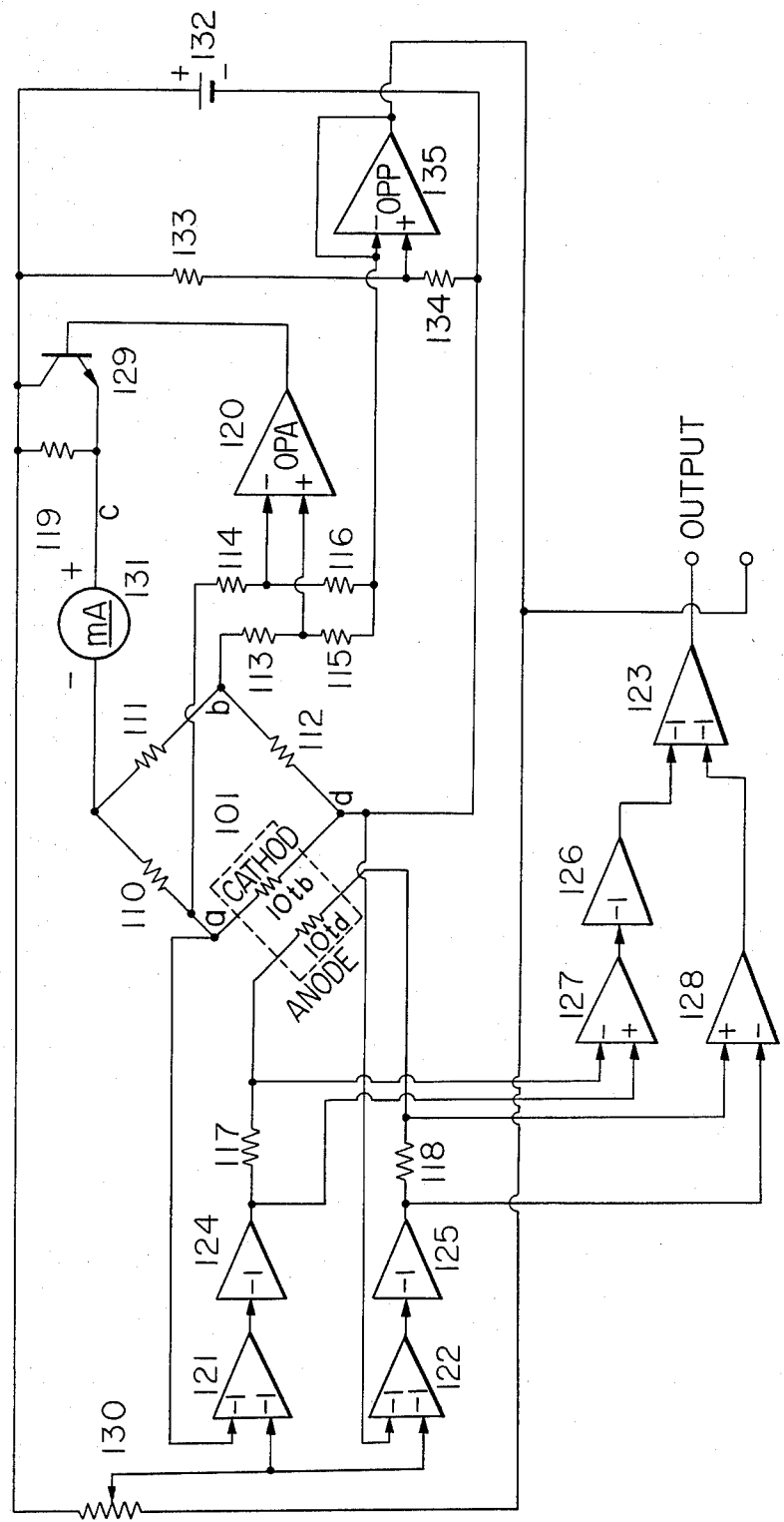
FIG. 47 is a circuit diagram of a limiting current type oxygen detector circuit with a constant temperature control circuit.

In order to keep the temperature of the limiting current type oxygen sensor constant, temperature detection must be performed. The resistance of the platinum electrode used as the heater may be utilized to detect the temperature as shown in FIG. 47. Alternatively, a method for detecting temperature using an internal resistance of an electrolyte (in Japanese patent application No. 56-78031) or a method for detecting temperature using another heat-sensitive element may alternatively be utilized.

FIG. 47 shows a limiting current type oxygen detector with a constant temperature control circuit.

The constant temperature control circuit keeps the sensor temperature constant even if heat dissipating conditions such as air flow rate are changed. With this constant temperature control circuit, the limiting current (oxygen concentration) can be highly precisely measured, and at the same time, only one power source is required.

Referring to FIG. 47, reference numeral 101 denotes a limiting current type oxygen sensor. The sensors 101X, 101Y, 101V and 101W can also be used for this purpose. A cathode 101b constitutes one of the sides of the Wheatstone bridge. Resistors 110 to 112 constitute the other three sides of the Wheatstone bridge. An output voltage of the bridge is divided by resistors 113 and 115 and by resistors 114 and 116. The divided voltages are supplied to an operational amplifier 120. An output voltage from a DC power source which is the only power source of the circuit is divided by resistors 133 and 134. One end each of resistors 115 and 116 is connected to a node of the resistors 133 and 134 or to an output terminal of an operational amplifier 135. If an allowable range of voltages supplied to the operational amplifier is wide, a voltage divider constituted by the resistors 113 and 115 and the resistors 114 and 116 may be omitted. In this case, the output from the bridge is directly coupled to the operational amplifier.

The output from an operational amplifier 120 is supplied to the base of a power transistor 129. A positive terminal of a power source 132 is connected to the collector of the power transistor 129. A positive terminal of an ammeter 131 is connected to the emitter of the power transistor 129. A resistor 119 is connected between the connector and emitter of the power transistor 129. The negative terminal of the ammeter 131 is connected to the node of resistors 110 and 111. The node between the heater/cathode 101b and the resistor 114 is connected to the negative terminal of the power source 132. The node between the resistor 110 and the heater/cathode 101b is connected to the resistor 114. The node between the resistors 114 and 116 is connected to a negative input terminal of the operational amplifier 120 The node between the resistors 111 and 112 is connected to the resistor 113. The node between the resistors 113 and 115 is connected to the positive input terminal of the operational amplifier 120. The positive terminal of the power source 132 is connected to the input terminal of a potentiometer (variable resistor) 130. An output of the variable resistor 130 is supplied to each one of input terminals of inverting adders 121 and 122. The node between the resistor 110 and the heater/cathode 101b is connected to the other input terminal of an inverting adder 121. An output from the inverting adder 121 is supplied to the input terminal of an inverter 124. An output from the inverter 124 is supplied to the heater/anode 101d through the resistor 117. An output from an inverter 125 is supplied to the other terminal of the heater/anode 101d through a resistor 118. The other input terminal of the inverting adder 122 is connected to the node between the heater/cathode 101b and the resistor 112. An output from the inverting adder 122 is supplied to the input terminal of the inverter 125. The node between the inverter 124 and the resistor 117 is connected to the positive input terminal of a differential amplifier 127. The node between the resistor 117 and the heater/anode 101d is connected to the negative input terminal of the differential amplifier 127. An output from the differential amplifier 127 is supplied to the input terminal of an inverter 126. An output from the inverter 126 is supplied to the input terminal of an adder 123. The node between the heater/anode 101d and the resistor 118 is connected to the positive input terminal of a differential amplifier 128. The node between the inverter 125 and the resistor 118 is connected to the negative input terminal of the differential amplifier 128. An output from the differential amplifier 128 is supplied to the input terminal of the adder 123. An output voltage of the inverting adder 123 with reference to the output voltage of the operational amplifier 135 is proportional to the limiting current (oxygen concentration). The reference input voltages of the inverting adders 121 to 123 and the inverters 124 to 126 are supplied from the operational amplifier 135 although not shown in the figure.

The mode of operation of the circuit will be described below. A potential at a point a differs from a potential at a point b, and a potential difference is multiplied by a coefficient (0.8 to 0.5) by a voltage divider. The resultant voltage is multiplied by the operational amplifier 120 with a high amplification factor of 10,000 to 100,000. If the output from the operational amplifier 120 is a large current, the resultant voltage described above can be directly supplied to a point c. However, in this embodiment, since the output current from the operational amplifier 120 is small, the power transistor 129 is connected to an emitter follower so as to amplify the current. The current flowing through the bridge is measured by an ammeter 131. The resistors 133 and 134 halve the voltage from the power source 132. A current corresponding to a divided voltage is amplified by the operational amplifier 135. With the above connections, a negative feedback control circuit is constituted. A potential difference between the points a and b reaches an equilibrium at a value which is obtained by dividing the output voltage of the operational amplifier 120 by the amplification factor. The value is substantially zero and the potentials at the points a and b may be regarded equal to each other in a practical sense. The equilibrium described above is obtained because the temperature coefficient of resistance of the heater/cathode 101b is great. When the temperature is increased by the input voltage, the resistance is increased.

The mode of operation of the circuit which controls the voltage to be applied to the heater/anode 101d will be described below. A limiting current measuring voltage is set by the variable resistor 130. The output voltage of the inverter 124 corresponds to a value obtained by adding the potential at the point a to the output voltage of the variable resistor 130. The output voltage of the inverter 125 corresponds to a value obtained by adding the potential at a point d to the output voltage of the variable resistor 130. A potential difference at any point between the heater/cathode and the heater/anode corresponds to the output voltage of the variable resistor 130. There is no effect on the current flowing through the heater/cathode.

The resistors 117 and 118 are limiting current detection resistors. A current flowing through the resistor 118 is smaller than a current flowing through the resistor 117 by the amount of current flowing from the heater/anode to the heater/cathode. The differential amplifiers 127 and 128 amplify a voltage dropped by the resistors 117 and 118. The output voltage of the differential amplifier 127 is decreased by the output voltage of the differential amplifier 128 by means of the inverter 126 and the adder 123.

Figure 48:
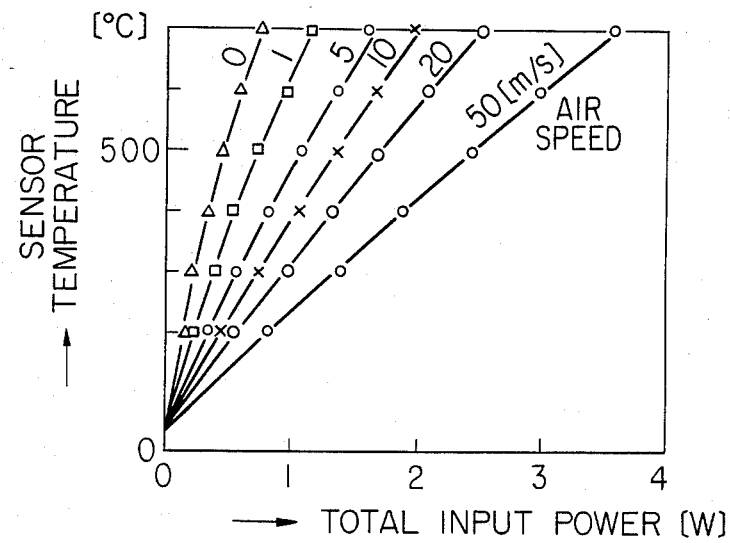
FIG. 48 is a graph showing the sensor temperature as a function of input power supplied to the anode/heater and the cathode/heater when the air speed of the limiting current type oxygen sensor of the present invention is used as a parameter.

The effects of the limiting current type oxygen sensor will be summarized below:

(1) Since the electrodes of the limiting current type oxygen sensor are directly heated, heat conduction is improved. FIG. 48 shows the relationship between the sensor temperature and the total input power to the heater/cathode and the heater/anode. Power loss is much decreased. For example, even at the high speed of 10 [m/sec], the sensor can be heated to a temperature of 700 [°C.] at power of 2 [W]. Thus, the power loss can be decreased to about 1/15 to 1/25 of the conventional power loss.

(2) When the constant temperature control is performed, the temperature variation is found to be 7 [°C.] under the variable air speed. Thus, excellent temperature stability is obtained.

Figure 49:
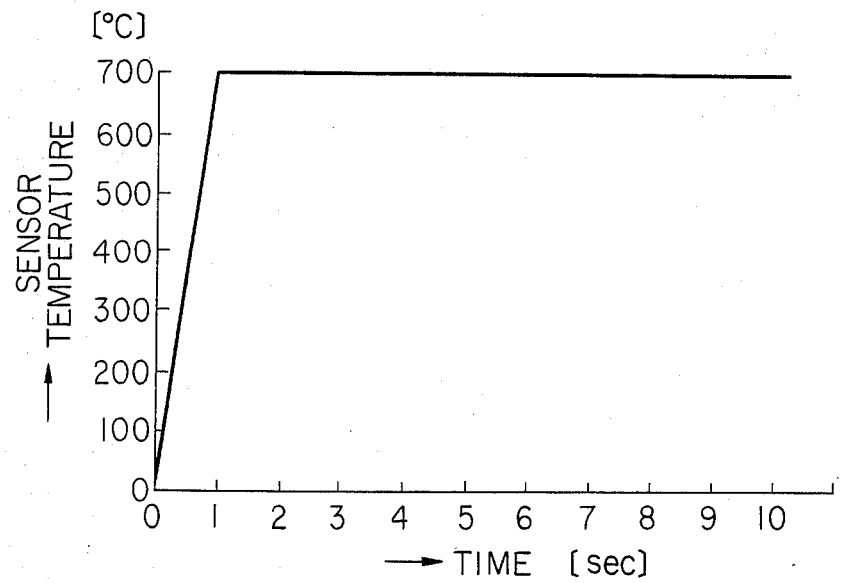
FIG. 49 is a graph showing the sensor temperature as a function of time after power is supplied by the constant temperature circuit.

(3) FIG. 49 shows the relationship between the time interval after the power switch is turned on and the sensor temperature when constant temperature control is performed. As is apparent from the figure, the sensor reaches the operating temperature in a very short period of time (1 [sec]) after the power switch is turned on.

(4) Since the heaters function as both the cathode or anode and the heat-sensitive elements, the construction of the sensor is very simplified, and the sensor can be manufactured at low cost.

(5) The oxygen concentration can be highly accurately measured from the initial period of operation to a period even when the gas flow is very fast. As a result, it is very effective to use the sensor according to the present invention so as to clean the exhaust gas, especially in the "cold start".

What is claimed is:

1. An oxygen sensor comprising an insulating substrate, a heater layer on a part of said substrate, said heater layer having a thickness of 0.2 µm to 20 µm and being made of a material selected from the group consisting of platinum, rhodium, palladium, and mixtures thereof, said insulating substrate having indentations which have a peak-to-peak thickness of up to 5 µm to provide bonding between said heater layer and said insulating substrate, and a further layer which has a thickness of about 0.01 µm to 1 µm and which is made of a material selected from the group consisting of aluminum, titanium, tungsten and molybdenum interposed between said insulating substrate and said heater layer so as to provide additional bonding therebetween.

2. A sensor according to claim 1, wherein said insulating substrate is of plate or hollow cylindrical shape.

3. A sensor according to claim 2, wherein said insulating substrate is made of a material selected from the group consisting of alumina, quartz, spinel, magnesia, zirconia, and mixtures thereof.

4. A sensor according to claim 1, further comprising a constant temperature control circuit means which detects resistance of said heater layer during heating for controlling power supplied to said heater layer to keep the resistance of said heater layer constant, whereby the heating temperature is kept constant.

5. A sensor according to claim 4, wherein said constant temperature control circuit comprises:
   a Wheatstone bridge which has a heater layer at one side thereof;
   an amplifier for amplifying an unbalanced voltage appearing at one of two pairs of opposing terminals of said Wheatstone bridge; and
   a circuit for controlling power supplied to the other one of two pairs of said opposing terminals of said Wheatstone bridge in accordance with the output from said amplifier.

6. A sensor according to claim 5, wherein said circuit for controlling power supplied to the other one of said two pairs of opposing terminals of said Wheatstone bridge, comprises:
   an intermittent control section having
      a sample holding circuit for holding the output from said amplifier so as to control power supply to said Wheatstone bridge by intermittently supplying the power in accordance with the output from said amplifier,
      a triangular wave oscillator,
      an adder for adding the output from said sample holding circuit and the output from said triangular wave oscillator, and
      a comparator for comparing a reference value with the output from said adder and for producing an ON/OFF signal; and
   a power transistor which is switched by an output from said intermittent control section.

7. A sensor according to claim 4, wherein said constant temperature control circuit comprises:
   a power source for supplying power to said heater layer;
   means for detecting current flowing from said power source to said heater layer;
   operating means for obtaining the electric resistance of said heater layer from the current detected by said current detecting means and from a voltage applied from said power source to said heater layer;
   an operational amplifier for amplifying a differential voltage between a predetermined preset voltage and the output voltage which is produced from said operating means and which represents the electric resistance of said heater layer; and
   a power transistor for controlling power supplied from said power source to said heater layer on the basis of the output from said operational amplifier.

8. A sensor according to claim 1 further comprising an oxygen partial pressure sensitive means on one major surface of said insulating substrate.

9. A sensor according to claim 8, wherein said oxygen partial pressure sensitive means comprises: a thin film made of a material obtained by adding a catalyst selected from the group consisting of platinum, rhodium, palladium and mixtures thereof to an oxide material selected from the group consisting of niobium pentoxide and cerium oxide; and a pair of electrodes mounted on said thin film.

10. A sensor according to claim 9, wherein each of said electrodes mounted on said thin film has a comb shape.

11. A sensor according to claim 9 wherein the amount of said catalyst added to said oxide material to form said thin film is within the range of 5 wt % to 40 wt %.

12. A sensor according to claim 1, wherein said heater layer is made of a mixture of platinum with one of rhodium and palladium, said one of rhodium and palladium being present in an amount of 0 to 60 wt %.

13. A sensor according to claim 1, wherein said heater layer has a band shape with a width of not more than 100 μm and is folded in a zigzag shape.

14. A sensor according to claim 1, further comprising a protective coating which has a thickness of 0.01 μm to 500 μm and which is made of a material selected from the group consisting of materials based on alumina, silica, spinel, magnesia, zirconia and mixtures thereof is formed on a surface of said heater layer.

15. An oxygen sensor as claimed in claim 1 having a cathode on one major surface of an oxygen ionic conductor, an anode on the other major surface of said oxygen ionic conductor, and means for controlling the rate of oxygen permeation into said oxygen ionic conductor, wherein the cathode and anode each comprises said insulating substrate, said heater layer and said further layer of the same size and shape; and two pairs of lead wires respectively connected to said cathode and anode so that said substrate and layers thereon respectively function as a heater/cathode (cathode/heater) and as a heater/anode (anode/heater).

16. A sensor according to claim 15 further comprising voltage applying neans for applying substantially the same voltage to said cathode/heater through one of said two pairs of lead wires and to said anode/heater through the other one of said two pairs of lead wires, and for applying a limiting current detection voltage across said cathode/heater and said anode/heater.

* * * * *